United States Patent
Oroskar et al.

(10) Patent No.: US 9,084,994 B2
(45) Date of Patent: Jul. 21, 2015

(54) APPARATUS AND METHOD FOR PARALLEL COLLECTION AND ANALYSIS OF THE PROTEOME AND COMPLEX COMPOSITIONS

(75) Inventors: Asha A. Oroskar, Oak Brook, IL (US); John P. LaCava, New York, NY (US); Michael Paul Rout, New York, NY (US); Anil R. Oroskar, Oak Brook, IL (US)

(73) Assignees: OROCHEM Technologies, Inc., Naperville, IL (US); The Rockefeller University, New York, NY (US)

( * ) Notice: Subject to any disclaimer, the term of this patent is extended or adjusted under 35 U.S.C. 154(b) by 728 days.

(21) Appl. No.: 13/199,811

(22) Filed: Sep. 9, 2011

(65) Prior Publication Data

US 2013/0065771 A1    Mar. 14, 2013

(51) Int. Cl.
*G01N 30/02* (2006.01)
*B01L 3/00* (2006.01)
*G01N 33/68* (2006.01)
*G01N 35/00* (2006.01)

(52) U.S. Cl.
CPC ........ *B01L 3/50255* (2013.01); *G01N 33/6803* (2013.01); *B01L 2200/0631* (2013.01); *B01L 2300/087* (2013.01); *B01L 2300/0829* (2013.01); *B01L 2400/0409* (2013.01); *B01L 2400/0487* (2013.01); *G01N 35/00* (2013.01)

(58) Field of Classification Search
USPC .......................................................... 506/7
See application file for complete search history.

(56) References Cited

U.S. PATENT DOCUMENTS

| | | | |
|---|---|---|---|
| 5,075,430 A | 12/1991 | Little | |
| 5,234,809 A | 8/1993 | Boom | |
| 5,650,506 A | 7/1997 | Woodard | |
| 6,864,100 B1 * | 3/2005 | Ribbe et al. | 436/178 |
| 8,247,545 B1 * | 8/2012 | Colpan | 536/25.4 |
| 2003/0180714 A1 | 9/2003 | Sidhu | |
| 2007/0087396 A1 * | 4/2007 | Konrath et al. | 435/7.92 |
| 2008/0287661 A1 * | 11/2008 | Jones | 530/418 |

(Continued)

OTHER PUBLICATIONS

Bostroem, M., et al., "Why forces between proteins follow different Hofmeister series for pH above and below pI", Biophysical Chemistry, 2005, vol. 11, pp. 217-224, Elsevier Ltd., The Netherlands.

(Continued)

*Primary Examiner* — Christopher M Gross
*Assistant Examiner* — Richard L Manteuffel
(74) *Attorney, Agent, or Firm* — Richard P. Silverman & Assoc., LLC

(57) ABSTRACT

This invention relates to a kit and a method for the collection and analysis of complex protein mixtures. More particularly, the invention relates to a kit comprising a single barrel filtration well or a multi-well filtration plate wherein each well comprises an upper filtration zone; a lower filtration zone; a conical flow director zone; and, an elution tip, wherein the upper filtration zone and the lower filtration zone are separated by a retainer ring disposed within the lower filtration zone. The upper filtration zone comprises an upper collection zone, a sponge zone, and a deep bed filtration zone; and, the lower filtration zone comprises the retainer ring, a supported hydrophilic membrane and a lower bed filtration media. When used with an array of selected buffer solutions, the multi-well filtration plate can provide accurate, automated, high-throughput protein analysis by affinity chromatography.

30 Claims, 10 Drawing Sheets

(56) References Cited

U.S. PATENT DOCUMENTS

2011/0312506 A1* 12/2011 von Specht ............... 506/2
2013/0196841 A1* 8/2013 Dobrowolski ............. 494/37

OTHER PUBLICATIONS

Chait, Brian T., "Laboratory of Mass Spectrometry and Gaseous Ion Chemistry: Immunoaffinity Purifications of Protein Complexes", 2006, <http://prowl.rockefeller.edu/protocols/ >, published on-line by The Rockefeller University, New York, NY.

Oeffinger, Marlene, et al., "Comprehensive analysis of diverse ribonucleoprotein complexes", Nature Methods, 2007, vol. 4, No. 11, 951-956, Nature Publishing Group, published on-line Oct. 7, 2007.

Javid, Nadeem, et al., "Protein-Protein Interactions in Complex Cosolvent Solutions", ChemPhysChem, 2007, vol. 8, pp. 679-689, Wiley-HCH Verlag GmbH & Co., Weinheim, Germany.

Kunz, W., et al., "Zur Lehr von der Wirkung der Salze (about the science of the effect of alts): Franz Hofmeister' historical papers", Colloid and Interface Science, vol. 9, 2004, pp. 19-37, Elsevier Ltd.

Kunz, W., et al., "The present state of affairs with Hofmeister effects", Colloid and Interface Science, 2004, vol. 9, pp. 1-18, Elsevier Ltd., The Netherlands.

Scheich, Christoph, et al., "An automated method for high-throughput protein purification applied to a comparison of His-tag and GST-tag affinity chromatography", BMC Biotechnology, 2003, vol. 3, No. 12, pp. 1-8, published on-line Jul. 28, 2003 <http://www.biomedcentral.com/1472-6750/3/12>.

Tadeo, Xavier, et al., "Protein Stabilization and the Hofmeister Effect: The Role of Hydrophobic Solvation", Biophysical Journal, Nov. 2009, vol. 97, pp. 2595-2603, Rockville, Maryland.

Williamson, Mike P. and Michael J, Sutcliffe, "Experimental Approaches to Protein-Protein interactions", Biochemical Society Transactions, 2010, vol. 38, pp. 875-878, Presented at Biochemical Society Focused Meeting held at Sheffield, U.K. Jan. 11-12, 2010.

Zhang, Yanjie, et al., "Interactions between macromolecules and ions: the Hofmeister series", Current Opinion in Chemical Biology, 2006, vol. 10, pp. 658-663, Elsevier Ltd., The Netherlands.

Pall Corporation, "IMAC Purification of Polyhistidine-tagged Protein Using the AcroPrepTM 96 Filter Plate", Jan. 2011, <http://site.pall.com/laboratory_34505.asp> published on-line by Pall Corporation, Port Washington, NY.

Frank Alber, et al., "The Molecular Architecture of the Nuclear Pore Complex", Nature, Nov. 29, 2007, vol. 450, pp. 695-701, Nature Publishing Group, New York, NY.

Giovanni Candiano, et al., "Blue silver, A very sensitive colloidal Coomassie G-250 staining for proteome analysis", Electrophoresis, 2004, vol. 25, pp. 1327-1333, Wiley-VCH Verlag GmbH, Weinheim, Germany.

Anne-Claude Gavin, et al., "Proteome survey reveals modularity of the yeast cell machinery", Nature, Mar. 30, 2006, vol. 440, pp. 631-636, Nature Publishing Group, New York, NY.

Anne-Claude Gavin, et al., "Functional organization of the yeast cell proteome by systematic analysis of protein complexes", Nature, Jan. 10, 2002, vol. 415, pp. 141-147, Macmillian Magazines Ltd, New York, NY.

Jordan J. Lichty, et al., "Comparison of affinity tags for protein purification", Protein Expression and Purification, 2005, vol. 41, pp. 98-105, Elsevier Inc., The Netherlands.

Dirk Linke, Methods in Enzymology, Detergents: An Overview (Chapter 34), 2009, vol. 463, pp. 603-617, Elsevier Inc., The Netherlands.

K. Terpe, "Overview of tag protein fusions: from molecular and biochemical fundamentals to commercial systems", Appl. Microbiol Biotechnol, published on-line Nov. 7, 2002, vol. 60, pp. 523-533, Springer-Verlag, Berlin, Germany.

Ina Poser, et al., "BAC TransgeneOmics: a high-throughput method for exploration of protein function in mammals", Nature Methods, vol. 5, No. 5, May 2008, pp. 409-415, published on-line, Nature Publishing Group, New York, NY.

Junmin Peng, et al., Evaluation of Multidimentional Chromatography Coupled with Tandem Mass Spectrometry (LC/LC-MS/MS) for large scale protein analysis, Journal of Proteome Research, 2003, vol. 2, pp. 43-50, American Chemical Society, Washington, D.C.

Rout, Michael P. "Immunoaffinity purifications of protein complexes", 2007, <http://www.ncdir.org/protocols.php>, published on-line by The Rockefeller University, New York, NY.

* cited by examiner

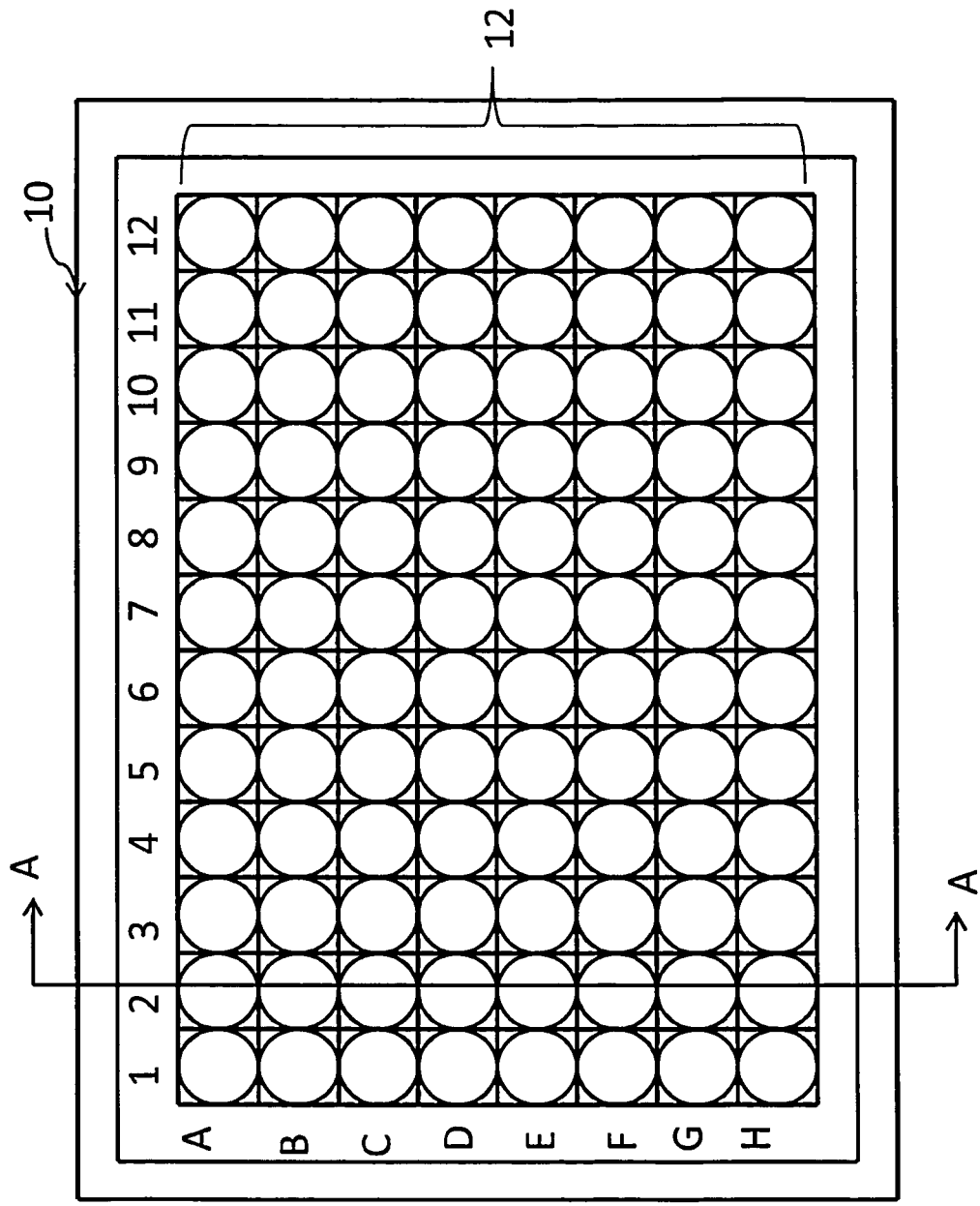

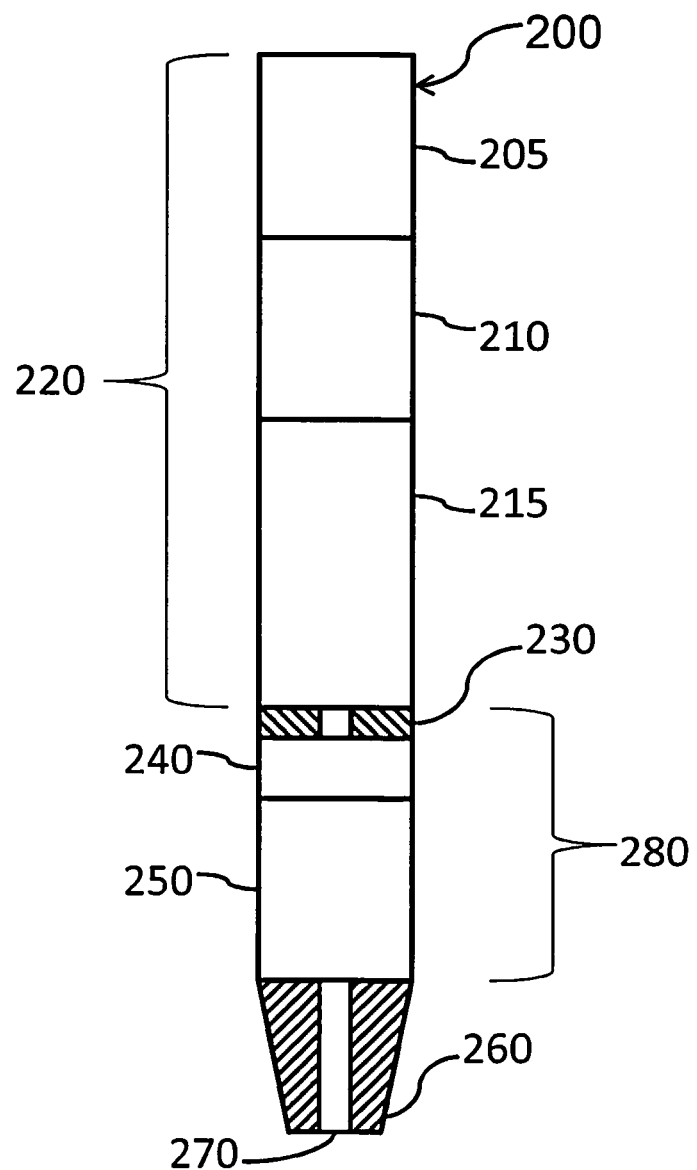

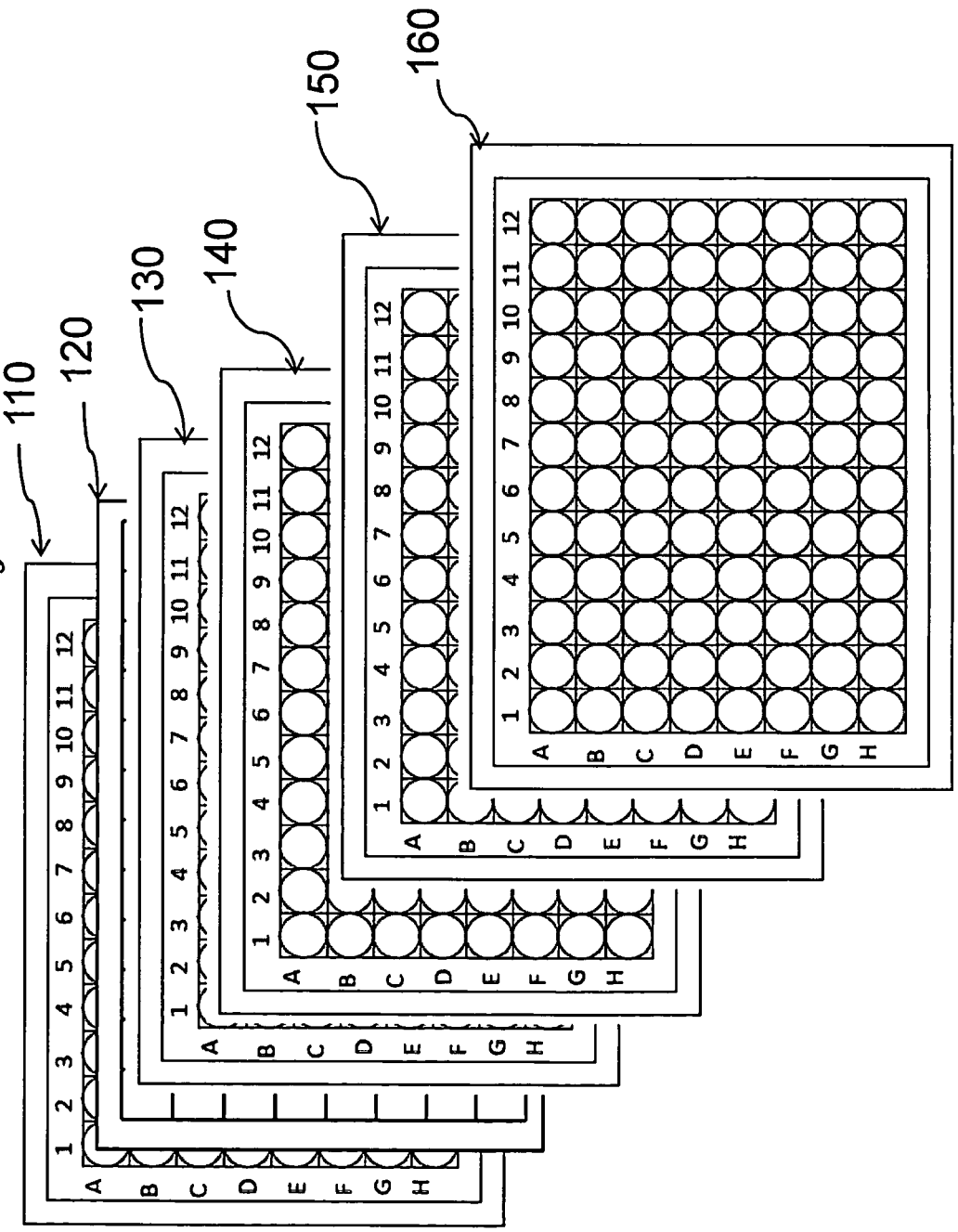

*Fig. 4*

| R/C | 1 | 2 | 3 | 4 | 5 | 6 | 7 | 8 | 9 | 10 | 11 | 12 |
|---|---|---|---|---|---|---|---|---|---|---|---|---|
| A | 125 A<br>15 H | 125 A<br>10 I | 125 A<br>5 J | 250 A<br>15 I | 250 A<br>10 I | 250 A<br>5 J | 500 A<br>15 H | 500 A<br>10 I | 500 A<br>5 J | 1500 A<br>15 H | 1500 A<br>10 I | 1500 A<br>5 J |
| B | 20 B<br>100 F<br>15 H | 20 B<br>500 F<br>15 H | 20 B<br>100 F<br>10 I | 20 B<br>500 F<br>10 I | 20 B<br>100 F<br>5 J | 20 B<br>500 F<br>5 J | 20 B<br>50 D<br>15 H | 20 B<br>50 D<br>20 F<br>15 H | 20 B<br>50 D<br>100 F<br>15 H | 20 B<br>50 D<br>500 F<br>15 H | 20 B<br>50 D<br>10 I | 20 B<br>50 D<br>20 F<br>10 I |
| C | 20 B<br>50 D<br>100 F<br>10 I | 20 B<br>50 D<br>500 F<br>10 I | 20 B<br>50 D<br>5 J | 20 B<br>50 D<br>20 F<br>5 J | 20 B<br>50 D<br>100 F<br>5 J | 20 B<br>50 D<br>500 F<br>5 J | 20 B<br>125 D<br>15 H | 20 B<br>125 D<br>20 F<br>15 H | 20 B<br>125 D<br>100 F<br>15 H | 20 B<br>125 D<br>500 F<br>15 H | 20 B<br>125 D<br>10 I | 20 B<br>125 D<br>20 F<br>10 I |
| D | 20 B<br>125 D<br>100 F<br>10 I | 20 B<br>125 D<br>500 F<br>10 I | 20 B<br>125 D<br>20 F<br>5 J | 20 B<br>125 D<br>100 F<br>5 J | 20 B<br>125 D<br>500 F<br>5 J | 20 B<br>250 D<br>5 J | 20 B<br>250 D<br>15 H | 20 B<br>250 D<br>20 F<br>15 H | 20 B<br>250 D<br>100 F<br>15 H | 20 B<br>250 D<br>500 F<br>15 H | 20 B<br>250 D<br>10 I | 20 B<br>250 D<br>20 F<br>10 I |
| E | 40 C<br>50 E<br>20 G<br>15 H | 40 C<br>50 E<br>100 G<br>15 H | 40 C<br>50 E<br>500 G<br>15 H | 40 C<br>50 E<br>10 I | 40 C<br>50 E<br>20 G<br>10 I | 40 C<br>50 E<br>100 G<br>15 H | 40 C<br>50 E<br>500 G<br>15 H | 40 C<br>100 G<br>10 I | 40 C<br>500 G<br>10 I | 40 C<br>100 G<br>5 J | 40 C<br>50 E<br>15 H | 40 C<br>50 E<br>20 G<br>15 H |
| F | 40 C<br>125 E<br>15 H | 40 C<br>125 E<br>20 G<br>15 H | 40 C<br>125 E<br>100 G<br>15 H | 40 C<br>125 E<br>500 G<br>15 H | 40 C<br>125 E<br>10 I | 40 C<br>125 E<br>20 G<br>10 I | 40 C<br>125 E<br>100 G<br>10 I | 40 C<br>125 E<br>500 G<br>10 I | 40 C<br>125 E<br>5 J | 40 C<br>125 E<br>20 G<br>5 J | 40 C<br>125 E<br>100 G<br>5 J | 40 C<br>125 E<br>500 G<br>5 J |
| G | 40 C<br>250 E<br>20 G<br>15 H | 40 C<br>250 E<br>100 G<br>15 H | 40 C<br>250 E<br>100 G<br>15 H | 40 C<br>250 E<br>500 G<br>15 H | 40 C<br>250 E<br>10 I | 40 C<br>250 E<br>20 G<br>10 I | 40 C<br>250 E<br>100 G<br>10 I | 40 C<br>250 E<br>500 G<br>10 I | 40 C<br>250 E<br>5 J | 40 C<br>250 E<br>20 G<br>5 J | 40 C<br>250 E<br>100 G<br>5 J | 40 C<br>250 E<br>500 G<br>5 J |
| H | 40 C<br>250 E<br>15 H | 40 C<br>250 E<br>20 G<br>15 H | 40 C<br>250 E<br>100 G<br>15 H | 40 C<br>250 E<br>500 G<br>15 H | 40 C<br>250 E<br>10 I | 40 C<br>250 E<br>20 G<br>10 I | 40 C<br>250 E<br>100 G<br>10 I | 40 C<br>250 E<br>500 G<br>10 I | 40 C<br>250 E<br>5 J | 40 C<br>250 E<br>20 G<br>5 J | 40 C<br>250 E<br>100 G<br>5 J | 40 C<br>250 E<br>500 G<br>5 J |

Fig. 8a
Snu71p
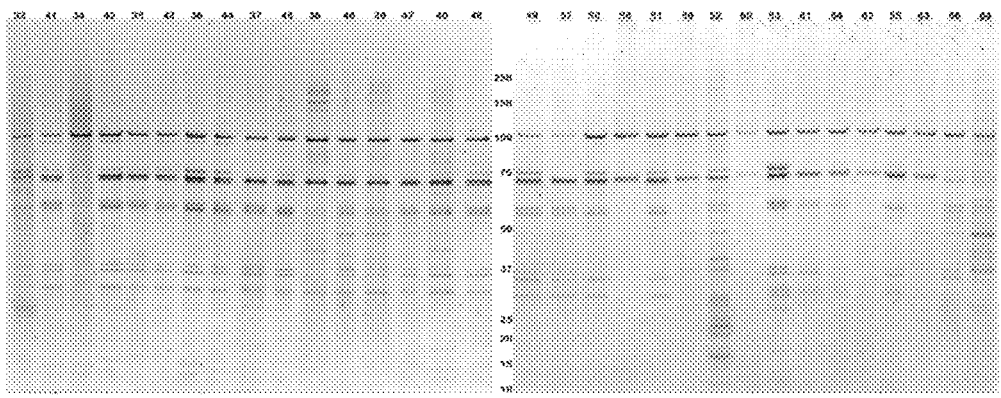
Csl4p
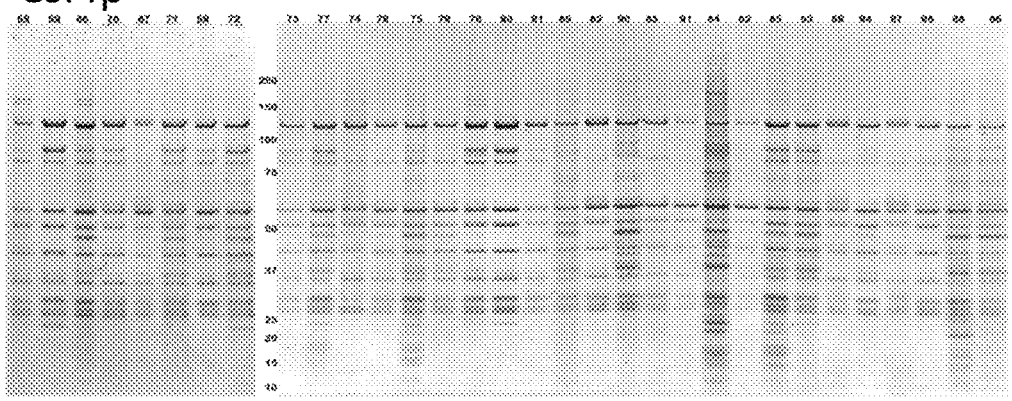
Arp2p
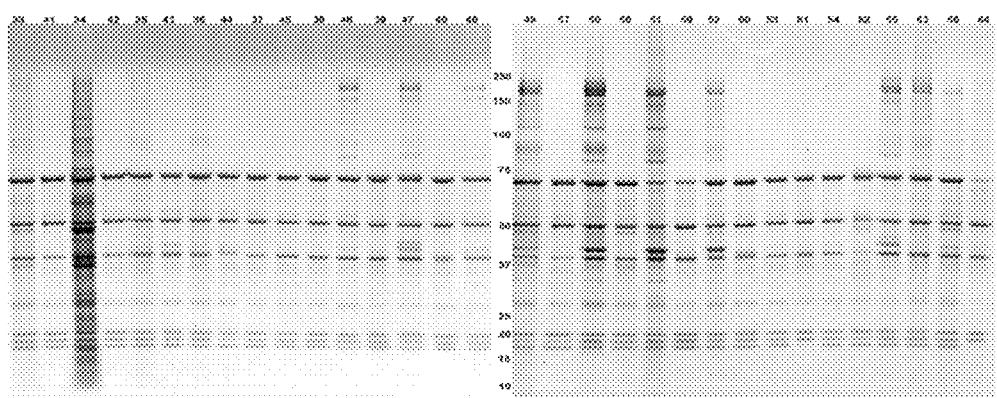

APPARATUS AND METHOD FOR PARALLEL COLLECTION AND ANALYSIS OF THE PROTEOME AND COMPLEX COMPOSITIONS

FIELD OF THE INVENTION

This invention concerns generally with an apparatus and a method for the parallel collection and analysis of complex protein mixtures. The method provides for the separation and the isolation of complex protein mixtures. More particularly, the invention relates to a kit comprising multifunctional reagents and a multi-layer filtration device that provides the simultaneous and parallel separation and isolation of complex protein mixtures.

BACKGROUND

The study of proteomics encompasses the study of individual proteins and how these proteins function within a biochemical pathway. Proteomics also includes the study of protein interactions, including how they form the architecture that constitutes living cells.

In order to isolate the individual proteins for the complex mixtures and characterize the properties on the proteins, techniques such as affinity chromatography are employed. Affinity chromatography is a method for separating protein mixtures and based on a very specific biological interaction, for example, interactions between an antigen and an antibody, or an enzyme and a substrate. Affinity chromatography entails the ability to design a chromatography that reversibly binds the protein to a known subset of molecules.

Protein complexes are now routinely immunoisolated from cell lysates via an affinity tagged member of the complexes. Affinity chromatography has become suitable for any organism for which there is an affinity handle for at least one of its proteins. This technology is widely used because of the relative ease of incorporating a genomic tag by homologous recombination, and also to the commercially available TAP-tag (tandem affinity purification) collection of dual affinity-tagged proteins. The immunoisolation technique is an exceptionally powerful method for rapidly and efficiently extracting a protein complex from cell lysate under conditions that attempt to preserve in vivo protein interactions.

US Patent Publication 2007/0077600A1, discloses that a common problem with the TAP-tag methods is the co-enrichment of proteins that associate non-specifically with affinity-tagged proteins. The 2007/0077600A1 publication proposes a method of determining whether or not associations between a given protein and other proteins in a cell are specific.

In an article entitled, "Experimental Approaches to Protein-Protein Interactions," by Mike P. Williamson and Michael J. Sutcliffe, it is disclosed that although there is an increase in demand for the high throughput analysis techniques like the TAP-tag method, these methods suffer from the problem that they depend on the formation of dilute solutions outside of the cell, and even though these methods employ mild interactions to isolate and purify individual proteins, weak interactions between proteins are lost. Generally, the intercellular environment is crowded, with protein occupying up to about 40 percent of the total fluid volume of the cell. Thus, within the cell, the protein-protein interactions will be stronger than they would be in dilute solution. Therefore, methods for purification outside the cell implies that weaker interactions will be lost.

Protein-protein interactions are typically identified and characterized by means of low-throughput biophysical methods. These biophysical methods may include nuclear magnetic resonance (NMR), crystallography, spectroscopic methods, chromatographic, mass spectroscopic, and calorimetric methods. Current methods are either low resolution and somewhat unreliable, or high resolution and low throughput.

There is also a need to develop technologies for analysis of the proteome that allow scaling up to industrial levels with the features of an industrial process: high accuracy, reproducibility and flexibility in that the process is high-throughput, automatable and cost-effective. There is a need to develop technologies that permit probing and identification of proteins in their native conformation using automated protocols and systems. In particular, there is a need to develop strategies and technologies for identification and characterization of hydrophobic proteins under physiological conditions.

This information can be gathered slowly in serial, or rapidly in parallel. Moreover, when this information is gathered in parallel, it has emergent-value related to the pattern of the information that is generally not obtained, or not equivalently obtained, in conventional serial fashion. Prior attempts for analysis of the proteome by affinity chromatography methods using a multi-well format have experiences problems in the stability of the well structure and uneven flow or plugging in the filter media.

It is desired to have a stable multi-well filtration system with uniform distribution of fluids throughout the multi-well filter when using centrifugation methods or positive pressure methods to provide the collection of interacting proteins in an affinity chromatography process.

SUMMARY

Applicant has discovered an apparatus and a method for the simultaneous and parallel collection and analysis of the proteome using a stabilized multi-well filtration device in combination with a structured array of buffer solutions in an affinity chromatography process. Applicant's stabilized well structure overcomes problems such as bed compression and filter media migration when the multi-well filtration device is employed with centrifugation or positive pressure methods to filter fluids through the multi-well filter. In addition, when applicant's multi-well filtration apparatus is employed in conjunction with a structured array of buffer solutions in an affinity chromatography process, the results are characterized by high accuracy and reproducibility. Furthermore, variations in the structured array of buffer solutions can provide flexibility in that the process can be adapted to high-throughput, automatable, and cost-effective proteome analysis.

In one embodiment, the present invention is a multi-well filter plate for the simultaneous and parallel purification and analysis of interacting proteins by affinity chromatography. The multi-well filter plate comprises a plurality of filtration wells. Each filtration well comprises an upper filtration zone, a lower filtration zone, a conical flow director zone, and an elution tip. The upper filtration zone and the lower filtration zone are separated by a retainer ring disposed within the lower filtration zone. The retainer ring permits fluid communication between the upper filtration zone and the lower filtration zone. The upper filtration zone comprises an upper collection zone, a sponge zone, and a deep bed filtration zone. The lower filtration zone comprises the retainer ring, a supported hydrophilic membrane, and a lower bed filtration media. Each of the filtration wells may be employed singly or disposed in generally rectangular arrays of 6, 24, 96, 192, and 384 total filtration wells, in arrangements of 2×3, 4×6, 8×12, 2(8×12), or 16×24 for use with centrifugation or with positive pressure.

In another embodiment, the present invention is a kit for the simultaneous and parallel purification and analysis of interacting proteins in an affinity chromatography process. The kit comprises at least one or more of the following:

a. a collection plate having an array of individual collection zones,
b. a buffer plate having an array of solvent reservoirs corresponding the array of individual collection zones in the collection plate,
c. a multi-well filter plate comprising a plurality of filtration wells, each filtration well being aligned with the array of individual collection zones of the collection plate, wherein each filtration well, comprises an upper filtration zone, a lower filtration zone, a conical flow director zone, and an elution tip, the upper filtration zone and the lower filtration zone being separated by a retainer ring disposed within the lower filtration zone, the retainer permitting fluid communication between the upper filtration zone and the lower filtration zone, said upper filtration zone comprising an upper collection zone, a sponge zone, and a deep bed filtration zone, the lower filtration zone comprising the retainer ring, a supported hydrophilic membrane, and a lower bed filtration media; and
d. a removable cover plate adapted to seal and cover the individual collection zones of the collection plate.

In a further embodiment, the invention is a process for the purification and analysis of interacting proteins in an affinity chromatography process. The process comprises:

dispensing a portion of cell powder granulates or cell pellets to be lysed to each individual collection zone of an array of individual collection zones in a first collection plate at an effective working temperature;

dispensing an array of solvents disposed in a buffer plate consisting of an array of corresponding solvent compositions aligned to correspond to the array of individual collection zones of the first collection plate into each individual collection zone;

covering the first collection plate with a removable cover plate adapted to sealably cover each individual collection zone and agitating the first collection plate to individually mix the cell powder granulates or cell pellets to be lysed in each individual collection zone with the array of solvent compositions to disperse and solubilize at least a portion of the cell powder granulates or pellets and provide an array of dispersed and at least partially solubilized protein material;

transferring a least a portion of the array of the dispersed and at least partially solubilized material from the first collection plate to a multi-layer filtration well in a first multi-well filter plate having a corresponding array of individual multi-layer filtration wells, each multi-layer filtration well being aligned with the array of individual collection zones of the collection plate, wherein each multi-layer filtration well, comprises an upper filtration zone, a lower filtration zone, a conical flow director zone, and an elution tip, the upper filtration zone and the lower filtration zone being separated a retainer ring disposed within the lower filtration zone, the retainer permitting fluid communication between the upper filtration zone and the lower filtration zone, the upper filtration zone comprising an upper collection zone, a sponge zone, and a deep bed filtration zone, the lower filtration zone comprising the retainer ring, a supported hydrophilic membrane, and a lower bed filtration media; and spinning the first multi-well filter plate at an effective centrifugation rate or pressurizing the upper collection zone to an effective pressure and collecting an array of filtrate in a second collection plate having an array of individual collection zones corresponding to the array of individual filtration wells and comprising affinity beads;

covering the second collection plate with a second removable cover plate adapted to sealably cover the individual collection zones of the second collection plate and batch binding the filtrate with the affinity beads to provide an array affinity tagged protein material bound to the affinity beads and unbound protein material;

washing the array of affinity tagged protein material bound to the affinity beads with the corresponding array solvent compositions to remove unbound protein material and to provide a slurry comprising an array of washed affinity tagged protein material bound to the affinity beads;

transferring the slurry of the washed array of affinity tagged protein material bound to the affinity beads in the corresponding array solvent compositions to a second filter plate and therein separating the array of washed affinity beads from the corresponding array solvent compositions and retaining said washed array of affinity beads comprising the affinity tagged protein material in the second filter plate to provide a retained washed array of affinity beads;

contacting the retained washed array of affinity beads with an elution solution and incubating the affinity tagged protein material bound to the affinity beads to interrupt the interaction between the affinity beads and the affinity tagged material; and centrifugating the second filter plate to provide an array of elution solution compositions comprising purified affinity tagged protein material in a second collection plate.

BRIEF DESCRIPTION OF THE DRAWINGS

FIG. 1 is an example illustration of a 96 well filtration plate, having a deep bed filtration zone of the present invention.

FIG. 2 is an example illustration of a single well of the multi-well filtration plate of the present invention.

FIG. 3 is an example illustration of an array of filtration plates and collection plates of the kit of the present invention.

FIG. 4 is an example illustration of a typical buffer array of capture solvents employed with the present invention.

DETAILED DESCRIPTION OF THE DISCLOSURE

Figure 1B:
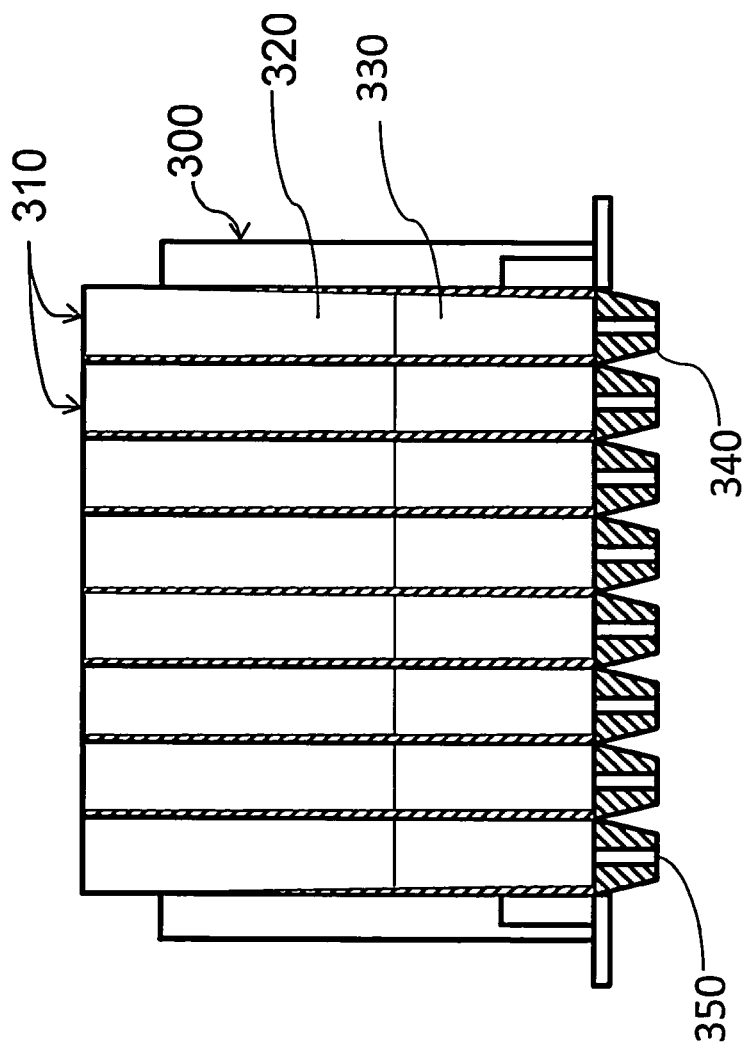
FIG. 1b is an example cross-sectional view of the 96 well filtration plate of the present invention.

Provided herein are methods and a kit for the simultaneous and parallel collection and analysis of the proteome on an industrial level in a high-throughput format. The methods and an apparatus or kit of the present invention permit sorting of complex mixtures of biomolecules. This invention provides a method to parallelize the process of affinity chromatography.

This process benefits from parallelization because it is necessary to determine the best conditions for the process empirically. While there are routine practices, and logical theoretical underpinnings to these practices, the theory is insufficiently comprehensive to guide even the expert in the art without additional information gathered by experimentation.

The present inventive concept pertains to expediting the time to arrive at best conditions for affinity chromatography processes—with consideration to the fact that the best conditions are not obvious and not generally able to be obtained through serial explorations. Moreover, best conditions are a plurality of conditions that may include any condition which results in the co-capture of interacting partner proteins (or other biomolecules) to the protein (or biomolecule) of interest; the affinity-tagged molecule. These conditions can include different conformations of the protein of interest: as a monomer or homomultimer, and more generally for the intention of affinity chromatography for proteomics applications, as heteromultimer (interacting with at least one other distinct protein), which may include a plurality of different heterodimers facilitated by the different conditions explored; each particular condition being best for that particular conformation of captured protein(s). It should be noted that best conditions are those where the result is considered to have a high signal to noise ratio for the captured conformation. That is, heterologous conformations should consist of physiologically relevant proteins to the protein of interest (part of the proteins bona fide interactome) and minimize the presence of non-physiological interactors. Often, affinity chromatography followed by mass spectrometry is the first mode of action to determine physiological vs. non-physiological interactors by proteomic means. Moreover, what is considered a high signal to noise ratio can often only be assessed relative to other results obtained in other conditions, requiring a broad exploration to begin to define this space.

Sample Preparation

According to the invention, a cell or biological material containing an affinity tagged molecule of interest is turned into a material suitable for dispensing into a multi-well format filter. The method comprises pulverizing a sample of cells, comprising a mixture of protein and other biomolecules, by grinding at a grinding temperature of −80° C. or lower, typically at temperatures reached by cooling with liquid nitrogen, for an effective grinding time to provide a grindate. Alternatively, cell pellets can be lysed and used as the cell material or grindate.

Solvents

Once the cell material or grindate is dispensed or placed into a multi-well first collection or first extraction plate, the grindate is exposed to solvent (extraction). The first extraction plate is maintained at the effective working temperature. There are many options for the selection of buffer solvents in the multi-well format. The selection of particular solvents will depend largely on the scope of the analysis desired. For example, each well is extracted in a different unique solvent. However, there are motivations for running samples in duplicate or greater, such as when only small quantities of material are retrieved, making analysis impossible except by pooling and combining the output of a given extraction. Hence, the method of the present invention does not explicitly constrain the way in which the extraction solutions are arrayed, only that cell material be placed in a multi-well format, and that an array of extraction solvent(s) in some combination be applied to that material. It is generally shown that the results attributed to a particular unique solvent can only be realized when the cell material is exposed only to that solvent during the extraction process. It is believed that extraction in one solvent, and then transfer to a second solvent, often yields different results.

Extraction Buffer Solvent Matrix Design

Fundamentally, the entire experimental design of the buffer array is exploratory. In cases of cellular and molecular biology, and of biochemistry, it is often crucial to establish the interaction networks of a protein of interest. Knowing these interactions will allow the researcher to understand in what cellular pathways the protein is involved and with what other protein molecules that protein interacts (directly and indirectly) to achieve its activity. In this manner, the cell's biology at the protein level is established To make a study of protein interactions comprehensive, the study must meet the following conditions:

a. Provide conditions of protein capture that are favorable for a broad array of different protein-protein interactions. Thus allowing the diversity of interactions formed by a given protein of interest to be captured intact, and be observed.

b. Results must be physiologically relevant. The purification procedure generates few artifacts and false positives while being of high sensitivity (i.e., favorable receiver operating characteristics).

It is believed that in developing the buffer solvent array, the major points to be considered in the selection of the particular buffer solvent array are buffer type and pH, salt type or types and ionic strength, how salts interplay with one another and with pH and detergent, and how detergents interplay with one another and with pH and salts.

The complexity of these buffer solvent systems is significant. The parameters are based on some theory, but primarily the screen for useful reagents and working conditions is empirical. The selection of the working pH of the affinity interaction used for protein capture is critical and will determine the buffer choice. This is typically from pH 6-8 (within the physiological range). Different buffers at the same pH and concentration have been observed to affect purification results, at least subtly. Preferably, the concentration of the pH buffer should generally be somewhere between 20-100 mM, and more preferably, the concentration of the pH buffer should generally be somewhere between 20-40 mM. Most particularly, the pH concentration should be at concentration which is effective to maintain the cell extract at the desired pH without altering the solvent conditions such that interplay between salts (and other salts) and detergents (and other detergents) are altered. The best guide is some modest amount more than the minimum amount of buffering agent required to assure sufficient buffering strength to equilibrate the pH of the dispersed and/or at least partially solubilized cell extract (which can often be acidic) to the desired working pH of the affinity chromatography. This assures a uniformly equilibrated pH across samples, and minimizes experimental variation within a buffer/pH condition explored.

Salts greatly influence many aspects of an extraction, including solubilization of cellular material into the solvent, as well as the protection or destruction of molecular conformation and intermolecular interfaces from solvent penetration (and therefore disruption). It is not believed to be important that salts are at "physiological" concentrations or even that the salt itself is "physiological." Moreover, the definition of physiological can be elusive, in addition to the fact that there is little innately physiological about the context of an affinity chromatography.

There are two classes of salts that are generally considered in this context: chaotropes and kosmotropes. It is generally expected that some optimal interplay between the two classes exists for any given purification. On the one hand there is the extraction, and prevention of nonspecific interactions forming in the artificial environment of the extract (i.e. outside the cellular milieu), usually the function of the chaotrope, and on the other hand there is the protection of physiological interactions from being themselves disrupted, usually the function of the kosmotrope. These can be two different salts (composed of 4 ionic parts between them), but even a single salt may often have one ionic component that is chaotropic, and another that is kosmotropic. There are generalities by which certain salts have been observed to be more or less generally stabilizing or destabilizing, and these generalizations can be heavily concentration dependant (not necessarily increasing/decreasing linearly). Many of these generalities are well represented by the Hofmeister series of anions and cations. This is a field under continuous development. The buffer solvent array of the instant invention can use only a single salt, but can also combine salts of a chaotropic nature with one of a kosmotropic nature, in varying proportions. The aim is to hit upon the critical combination for best signal to noise in a given purification.

Detergents can also greatly affect the outcome of an extraction of biological material and can be included in the buffer solutions. Detergents participate extensively in the prevention of non-specific binding of proteins to one another outside of the cellular milieu; they stabilize proteins with hydrophobic regions present at the solvent interface, and they can extract membrane bound proteins—transferring them from the insoluble to the soluble fraction of an aqueous-phase extraction. There are several classes of detergents, generally speaking there are nonionic, ionic (+ or – charged), and zwitterionic—each class has particular general properties, but their effects on an extraction are not necessarily immediately obvious. Similarly, mixing detergents results in new properties not immediately obvious. Finally, the effects of detergents on the system will be affected by the pH and the salt type(s) and concentration as well.

There are a number of other potential additives or reagents which share distinct and related properties with the above components of the buffer solutions. These reagents and their interplay are tools by which some unknown or poorly defined aspects of the intracellular milieu are replicated, resulting in the capture of protein interactions that require that milieu to remain sufficiently stable for affinity capture. Since the milieu of the cell is not monolithic, often many conditions must be screened, empirically, to find the regions where different types of protein interactions are extracted and stabilized in order to be captured and visualized. The example of a buffer solvent array of extraction solvents in a 96-well format employed in the present invention is shown in FIG. 4, and described hereinbelow. The buffer array of FIG. 4 provides one embodiment of a platform for the screening method of the present invention. The buffer array of FIG. 4 has three basic characteristics. Three pH levels 7.0, 7.4, and 8.0 are represented by three buffering agents: Ammonium Acetate, Hepes, or Tris (See table below.), respectively.

| Abbreviation | Chemical Name |
| --- | --- |
| AmAc, pH 7 | Ammonium Acetate, $CH_3COONH_4$ |
| HEPES, pH 7.4 | 4-2-hydroxyethyl-1-piperazine ethane sulfonic acid |
| Tris, pH 8 | Tris(hydroxymethyl)methylamine |
| KOAc | Potassium Acetate, $CH_3CO_2K$ |
| Na3Cit | Trisodium Citrate |
| KCl | Potassium Chloride |
| NaCl | Sodium Chloride |
| TRITON X-100* | Polyethylene glycol mono [4-(1,1,3,3-tetramethylbutyl) phenyl] ether |
| TWEEN 20** | Polyoxyethylene-20-sorbitane monolaurate |
| CHAPS | 3-[(3-cholamidopropyl) dimethylammonio]-1-propanesulfonate |

*TRITON X-100 (Available from Acros Organics)
**TWEEN 20 (Available from Fisher BioReagents)

Amongst these buffering agents, Ammonium Acetate (a moderate kosmotrope), being both a buffer and a salt was varied by concentration. In the case of Hepes, a marginal kosmotrope (KCl) was mixed with a moderate kosmotrope (K-Acetate). In the case of Tris, a marginal chaotrope (NaCl) was mixed with a strong kosmotrope (Na-Citrate). In all cases, three detergents were tested: a strong non-ionic detergent (TRITON X-100, Available from Acros Organics) and mild non-ionic detergent (TWEEN 20, Available from Fisher BioReagents), and a zwitterionic detergent (CHAPS).

Employing the exploratory method of the instant invention, more complete sets of interacting partners were discovered in a single week compared to similar discoveries of interacting partners which required years to produce employing serial testing methods. The current design of the buffer solvent array has been refined over several trials, but is by no means a final or static solution. The composition of the matrix is expected to grow as new conditions are discovered/tested. Since there are a finite number of wells, a user will have to select some initial broad composition, and refine the array further based on experimental results. On the other hand, if initial data exists, the buffer array of solvents can be established around the parameters for co-purifying known interacting partners as a starting point.

Solubilize Proteins in Array of Solvents

Hence, cell material, such as grindate or cell pelles to be lysed (disrupted), is distributed to a multi-well plate. Generally, the cell grindate or the cell pellets to be lysed is dispensed to a collection plate at an effective working temperature of from −80 to 37° C., and preferably the cell grindate or the cell pellets to be lysed is dispensed to a collection plate at an effective working temperature of from −80 to 25° C. The dispensed cell grindate or cell pellets to be lysed is then exposed to an array of unique buffered solvents respectively in individual collection zones in a collection plate. The buffered solvents comprise at least one ingredient such as a salt, a detergent, or a buffering compound in water. According to the current invention, the collection plate containing the cell grindate of cell pellets to be lysed and a buffer solution from the array of buffered solvents is covered and agitated to disperse and at least partially solubilize the protein material. Dispersal of the cell material or grindate can be achieved in any well-know manner, such as covering and mechanically agitating the covered collection plate, or applying ultrasonic energy—directly, or indirectly to the covered collection plate in a water bath maintained at the effective working temperature.

The cell materials exposed to the solvents then comprise mixtures of soluble and insoluble materials unique to each solvent, respectively. For best results, it is important to separate soluble extracted material from insoluble material. If this is not done, a low signal to noise ratio, relative to purification in the same solvent conducted without separation of soluble and insoluble material, will be realized. In some cases the result may not be obtained at all without the initial separation of insoluble material, and the affinity chromatography may simply fail. Typically, separation is accomplished in single filtration tubes containing a single filtration media by centrifugation under high centrifugal forces. Generally high speed centrifugation rates of about 15,000 g or higher are accepted as standard.

Filter well formats of a single barrel filtration well, and a multi-well format of 6 wells, 24 wells, 96 wells, 192 or 384 wells is preferred. Such multi-well filter plates may comprise 2×3, 4×6, 8×12, 2(8×12), or 16×24 rectangular arrays of the single barrel filtration wells. These rectangular arrays may be composed of appropriate numbers of single barrel filtration wells adapted to be disposed in the preferred rectangular arrays. However, the method is not restricted explicitly to this form of cell material or to this precise number of sample wells as a format. Lesser sample-well formats restrict the parallelization (or throughput) of the method, where as greater sample-well formats (if plate size is held constant) are constrained by quantities of input cell material and liquid volume that can fit in the wells. More sensitive output detection methods can facilitate an easy use of this method with less material and greater sample-well formats with the same plate size.

Affinity Chromatography Separation

The cell materials exposed to the solvents then comprise mixtures of soluble and insoluble materials in the collection plates is transferred to a single barrel filtration well or multi-well filter plate apparatus of the instant invention. In the single barrel filtration well or multi-well filter plate the insoluble materials are retained in the single barrel filtration well or multi-well filter plate and the filtrate is collected in a second collection plate. The second collection plate has an array of individual collection zones which correspond to the position and number of filter wells in the multi-well filtration plate. Each individual collection zone of the second collection plate contains affinity beads. The filtration step is facilitated by subjecting the filtration well(s) to centrifugation or by the applying positive pressure to carry out the filtration in a time period of less than about 5 minutes. In the instant method, as it is not possible nor practical to expose a 96-well format microtiter plate to a centrifugation at a relative centrifugal force (RCF) of 15,000 or greater, because the plate construction materials do not usually withstand this force and common centrifugal adapters for this form and force are not readily available. Surprisingly, the present invention overcame the problem of separation of the soluble extract from the insoluble material in the microtiter format by the development of a deep bed filtration kit which permitted acceptable separations using an effective centrifugation rate preferably at levels of 5,000 RCF or less. More preferably, the effective centrifugation rate of the present invention is a low speed centrifugation rate of between about 1500 and 2500 g. Optionally, an effective positive pressure of from 40 to 50 psig applied to the upper filtration zone of each filtration well may be employed. Various combinations and a wide variety of filtration materials were considered which would meet the following specifications:

low liquid retention low adsorption of protein give a result comparable or superior to high speed centrifugation Centrifuge and Collect Filtrate After transfer of the mixed extract to the filter, the dispersed and at least partially solubilized cell material is passed through the filter plate. This is currently achieved by low-speed centrifugation, but this could also be achieved by the application of positive pressure. The solution that passes through the filter (filtrate) is deposited into the second collection plate onto the affinity resin material. The insolubles are trapped in the filter and the filter is discarded.

Batch Binding/Incubation

The collection plate with filtrate and affinity beads are then incubated in a process referred to as batch binding—when the affinity tagged molecule is allowed time to bind to its binding partner while mixing. This step is routinely carried out at 4° C., which generally stabilizes protein interactions and minimizes protease catalyzed sample degradation.

After batch binding, the solution must be removed from the affinity resin. That is, the unbound liquid material removed from the beads. This is easily accomplished using magnetic beads, or more particularly super-paramagnetic beads, as employed in the process of the present invention. Accordingly, the collection plate, following batch binding, is placed onto a magnet designed for 96-well collection plates. The magnetic field causes the magnetic beads to adhere to the side of the collection plate. The remaining solution is removed by pipetting. After the removal of the solvent, the magnetic beads are washed with several changes of the same buffer solution in which they were extracted to remove the remaining unbound liquid material. Optionally, non-magnetic affinity beads may be employed. When non-magnetic affinity beads are employed, after the batch binding step, the bound non-magnetic beads are washed and separated from separated from the unbound material in the conventional manner, for example by centrifugation.

Transfer of Washed Beads to Second Filtration Zone

After washing, the beads are transferred to a second filtration zone. The liquid used to transfer the batch bound affinity beads is spun through second filtration zone, constituting a final wash, and leaving the beads deposited on the surface of the membrane in the second filtration zone. An elution solution is added to the batch bound beads in the second filtration zone, and the batch bound beads are held in the elution solution while mixing for some time to permit incubation. During this period, the interaction between the affinity tagged protein and the batch bound beads is interrupted by the elution solution. The elution solution is also of a generally denaturing character (such as a solution containing SDS or urea etc.), although a native elution using a reagent that disrupts specifically the affinity-tag interaction, leaving other physiological interactions intact, is also perfectly feasible in this approach.

Centrifugation and Recovery

After the incubation period, the filter plate is transferred to a new collection plate and the elution solution is collected by centrifugation. The filter plate retains the beads and is discarded. The eluted material can then be subjected to downstream interrogation by molecular analytical processes. Examples include SDS-PAGE, liquid chromatography (gel filtration, ion exchange, etc.), differential centrifugal sedimentation, or other standard and custom molecular techniques. In the context of proteomics, SDS-PAGE and mass spectrometry (MS) or LC-MS/MS sequencing, directly, would be used to characterize the composition of the sample.

The results are several-fold:

a comprehensive collection of purification standards, including best conditions;

an understanding of network of interactions formed by the protein of interest (its interactome under the conditions examined); and, a cross-reference between the conditions of isolation and the resulting isolated proteins (proteome)—informing the researcher about the physicochemical properties of the isolated protein.

DESCRIPTION OF THE DRAWINGS

FIG. 1 illustrates an example of the top view of a multi-well format multi-well filter plate 10 having a deep bed filtration zone of the present invention. The number of individual well is illustrated with a 96-well arrangement, although any number of individual wells may be incorporated into the multi-well filter plate 10 of the present invention depending upon the desired sample size and the capacity of centrifugation and solution dispensing equipment. Each of the individual wells are isolated from the adjacent well. The multi-well format multi-well filter plate 10 comprises a plurality of individual filter wells 12. Further details of the structure of a 96-well format multi-well filter plate will be discussed with reference to FIG. 1b which represents a side cross-sectional view at cross-section A-A on FIG. 1. Referring to FIG. 1b, the filter plate body 300 contains a plurality of individual filter wells 310. By way of example, each filter well has an upper filtration zone 320 and a lower filtration zone 330. Between the upper filtration zone 320 and the lower filtration zone 330, a support means is provided to support a retainer ring (not shown). The support means may be any mechanical means to support the retainer ring including a ridge or lip; or the upper filtration zone 320 may have a different geometry (e.g., square, triangular, or cylindrical) than the lower filtration zone 330, such as the upper filtration zone 320 having a square cross-sectional area and an open upper end, and the lower filtration zone 330 having a cylindrical cross-sectional area. Each individual filter well has conical flow director zone 340 and an elution tip 350, such that the upper filtration zone 320 is in fluid communication with the lower filtration zone 330, and the lower filtration zone is in fluid communication with the conical flow director zone 340 and the elution tip 350.

FIG. 2 is a simplified drawing of a single barrel filtration well or an individual filtration well 200 in the 96-well format multi-well filter plate having a deep bed filtration zone of the present invention. The multi-well filter plate comprises a plurality of the individual filtration well 200. Each filtration well is aligned with the array of individual collection zones of a collection plate (not shown). The filtration well comprises an upper filtration zone 220, a lower filtration zone 280, a conical flow director zone 260, and an elution tip 270. The upper filtration zone 220 has a square cross-section, and the lower filtration zone 280 has a cylindrical cross-section. The upper filtration zone 220, a lower filtration zone 280, a conical flow director zone 260, and an elution tip 270 are in fluid combination such that fluid may flow from the upper collection zone 205 through the elution tip 270 when positive pressure is applied to the upper collection zone 205, or when the multi-well filter plate is subjected to centrifugation forces up to or equal to about 5,000 RCF. A retainer ring 230 is disposed within the lower filtration zone 280 such that the retainer ring permits fluid communication between the upper filtration zone 220 and the lower filtration zone 280. The upper filtration zone 220 comprises an upper collection zone, 205, a sponge zone 210, and a deep bed filtration zone 215. The lower filtration zone 280 comprises a membrane 240 and a lower bed filtration media 250. The upper collection zone 205 provides a holding space of between 1-2 ml in a 96-well format. Preferably, the upper collection zone 205 has a void space volume of from 600 to 1200 mL (microliters). More preferably, the upper collection zone has a void space volume of from 750 to 1000 mL. The sponge zone 210 provides a depth filter with a tortuous path to filter coarse particles of proteins and fragments. The sponge zone comprises a filter media selected from the group consisting of polyester, polyethylene, glass fiber, PTFE, polypropylene, polycarbonate, and mixtures thereof. The deep bed filtration zone 215 comprises a deep bed filter matrix effective to provide for removal of insoluble protein fragments from a mixture of interacting proteins, insoluble protein fragments disposed in a buffer solution. Preferably, the deep bed filter matrix has a high surface area for filtration of small particles and has a particle size of from about 5 to about 105 um. More preferably, the deep bed filter matrix with a high surface area for filtration of small particles has a particle size of from about 5 to about 25 um. The deep bed filtration zone 215 comprises a deep bed filter media selected from the group consisting of diatomaceous earth, silica, activated carbon, FLORISIL (activated magnesium silicate, available from U.S. Silica Company, Berkeley Springs, W. Va.), glass wool, zeolites, and mixtures thereof. Preferably, the deep bed filtration zone 215 comprises diatomaceous earth and has a particle size of from about 5 to about 105 um, preferably 5 to 25 um. The retainer ring 230 prevents channeling of lysates and bypass through the deep bed filtration zone 215 and provides flow distribution and protects the membrane 240 from dislocation thus preventing the migration of particles from the deep bed filtration zone 215 into the filtrate. The retainer ring 230 is an o-ring or a screen comprising polypropylene or polyethylene. The supported hydrophilic membrane 240 provides a final clean up of the filtrate with essentially no non-specific binding of proteins. The supported hydrophilic membrane 240 comprises a membrane media selected from the group consisting of hydrophilic PVDF, hydrophilic PTFE, hydrophilic polyethylene, and combinations thereof. Preferably, the supported hydrophilic membrane 240 comprises polyester with hydrophilic PVDF or polypropylene with hydrophilic PVDF to provide a hydrophilic membrane porosity of from 0.2 to 1.2 um. More preferably, the hydrophilic membrane porosity of the supported hydrophilic membrane 240 is about 0.2 to about 0.45 um. The lower bed filtration media 250 provides membrane support and is selected from the group consisting of polyester, polyethylene, glass fiber, PTFE, polypropylene, polycarbonate, and mixtures thereof. Optionally, a second retainer ring (not shown) can be disposed between the supported hydrophilic membrane 240 and the lower bed filtration media 250 to provide additional support to the supported hydrophilic membrane 240.

FIG. 3 illustrates an array of filtration plates and collection plates comprising the kit of the present invention for the collection and analysis of the proteome on an industrial level in a high-throughput format. The kit comprises:

a. a first collection plate 110 for the deposition of the cell grindate, b. a removable cover plate 120 adapted for sealing and covering the first collection plate during the agitation of the first collection plate to solubilize the protein following the dispensing of the selected array of solvents to the first collection plate, c. a 96-well format multi-well filter plate 130 having a deep bed filtration zone of the present invention to separate the soluble cell material from the insoluble material, d. a second collection plate 140 for collecting the filtrate from the 96-well format multi-well filter plate 130 and for the deposition of the affinity beads, e. a second filtration plate 150 for retaining the affinity beads during the washing steps and the elution and incubating steps of the process of the present invention, and f. a third collection plate 160 for collecting the purified interacting proteins having been separated from the insoluble protein fragments, or fragments of insoluble cellular debris.

FIG. 4 illustrates a buffer plate having a typical array of selected solutions which are arrayed in a 96-well or 96-cell format to facilitate their use with the 96-well format multi-well filter plate having a deep bed filtration zone of the present invention. The solvents may be selected for parallel analysis or multiples of parallel analysis. The individual buffer compositions may be varied according to the objectives of the analysis, or varied according the amount of protein sample required for follow on analysis steps. As illustrated in FIG. 4, the components of the individual buffer solutions in a 96-well array is indicated by the symbol (A-J) for the buffer components shown in Table 1 hereinbelow:

TABLE 1

Components of Buffer Array

| Symbol | Abbreviation | Chemical Name |
|---|---|---|
| A | AmAc, pH 7 | Ammonium Acetate, $CH_3COONH_4$ |
| B | HEPES, pH 7.4 | 4-2-hydroxyethyl-1-piperazine ethane sulfonic acid |
| C | Tris, pH 8 | Tris(hydroxymethyl)methylamine |
| D | KOAc | Potassium Acetate, $CH_3CO_2K$ |
| E | Na3Cit | Trisodium Citrate |
| F | KCl | Potassium Chloride |
| G | NaCl | Sodium Chloride |
| H | TRITON X-100* | Polyethylene glycol mono [4-(1,1,3,3-tetramethylbutyl) phenyl] ether |
| I | TWEEN 20** | Polyoxyethylene-20-sorbitane monolaurate |
| J | CHAPS | 3-[(3-cholamidopropyl) dimethylammonio]-1-propanesulfonate |

*TRITON X-100 (Available from Acros Organics)
**TWEEN 20 (Available from Fisher BioReagents)

The buffer compositions shown in each well or cell of the 96-well buffer array shown in FIG. 4 are expressed in the concentration of individual components in milimolarity (mM); that is, each row specifies a complete buffer solvent with the concentration of each component specified in each cell. In practice, the particular solvents and the number of multiples in the buffer array will be selected by those skilled in the art in response to the results of the proteome analyses and the observed affinity of the desired interactions between the selected solvents and the protein complexes.

Figure 5:
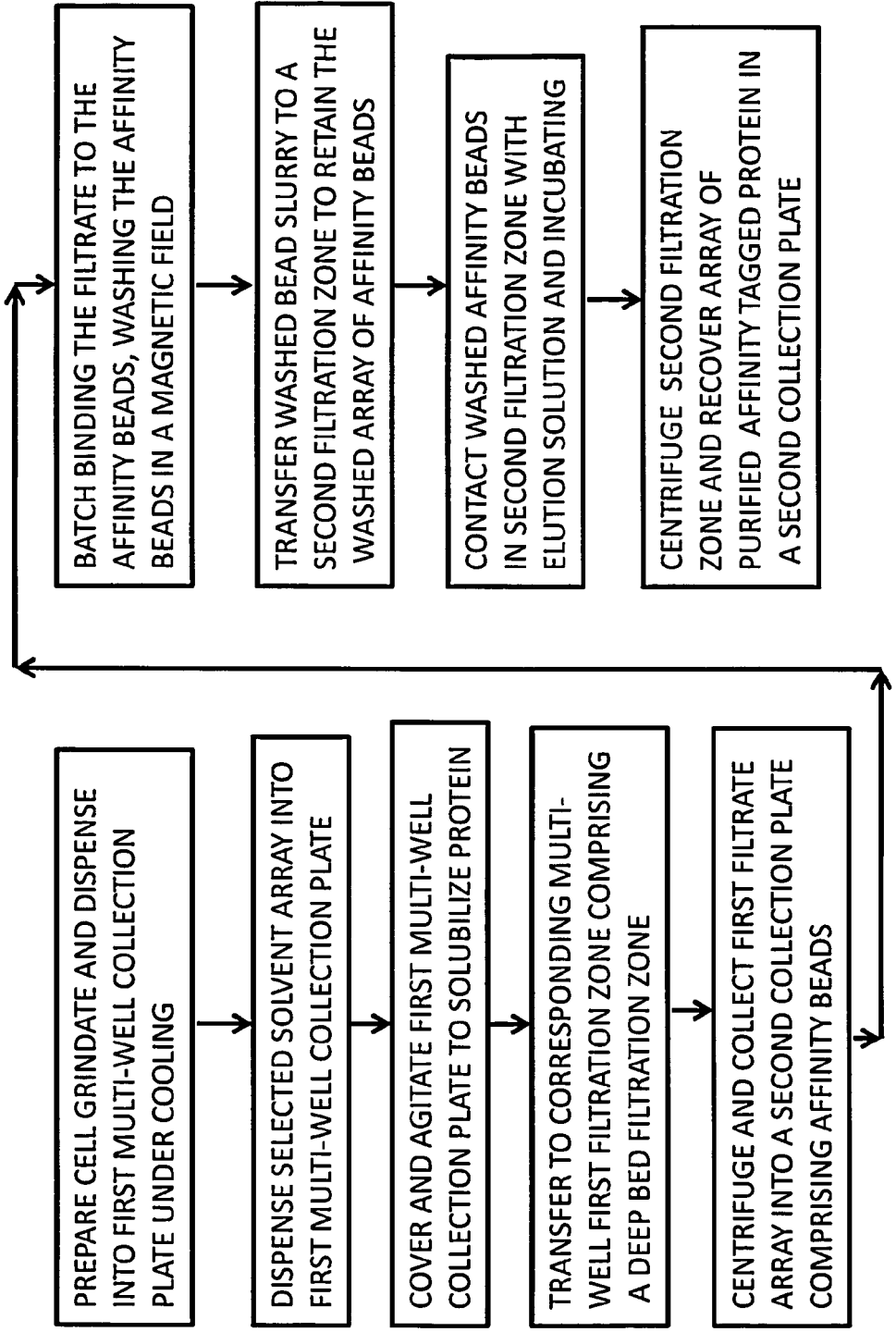
FIG. 5 is an example process flow diagram of an embodiment of the process for the purification and analysis of interacting proteins in an affinity chromatography process of the present invention.

FIG. 5 is a simplified process flow diagram illustrating the steps of the purification process described hereinabove. The steps of the process are as follows:
A. Prepare cell grindate and dispense the grindate powder into first multi-well collection plate under cooling;
B. Dispense the selected solvent array individually into first multi-well collection plate;
C. Cover and agitate first multi-well collection plate to solubilize protein in the solvents;
D. Transfer the solubilized grindate into an array of corresponding multi well first filtration zone comprising an array of deep bed filtration zones;
E. Centrifuge and collect first filtrate array into a second collection plate, each segment of which comprises affinity beads;
F. Batch binding the filtrate to the affinity beads and washing the affinity beads in a magnetic field;
G. Transfer washed bead slurry to a second filtration zone to retain the washed array of affinity beads;
H. Contact washed affinity beads in second filtration zone with elution solution and incubating; and,
I. Centrifuge second filtration zone and recover array of purified affinity tagged protein in a third collection plate.

The following examples are provided to illustrate the present invention and are not intended to limit the scope of the claims that follow.

EXAMPLES

Example 1

A comparison of the efficacy of a series of filter types of the present invention in a test spin column format with centrifugation was prepared. With reference to FIG. 2, the combination of the components of each zone (Sponge Zone 210, Deep Bed Filtration Zone 215, Retainer Ring 230, Membrane Zone 240, and Lower Bed Filtration Media Zone 250) of the individual filtration wells is shown hereinbelow in Table 2 for well filter types A through M.

TABLE 2

Individual Well Structure Types A-M

| Well No. | Sponge Zn | Deep Bed Filtration Zn | Ret. Ring | Membrane Zn | Lower Bed Filtration |
|---|---|---|---|---|---|
| A | Polyester | Acidic Alumina | None | Glass Fiber | Polyester |
| B | Polyester | Acidic Alumina | None | 90um PE | None |
| C | Polyester | Alumina Neut. | None | Glass Fiber | None |
| D | Polyester | Alumina Neut. | None | 90um PE | None |
| E | Polyester | Diatom. Earth | None | 90um PE | None |
| F | Polyester | Diatom. Earth | None | Glass Fiber | Polyester |
| G | Polyester | Diatom. Earth | None | None | Polyester |
| H | Polyester | Glass Wool | Regen Cellulose | None | Polyester |
| I | Polyester | Silica Gel | None | PVDF | Polyester |
| J | Polyester | Silica Gel | None | None | Polyester |
| K | Polyester | Silica Gel | None | 90um PE | None |
| L | Polyester | Silica Gel | None | Glass Fiber | None |
| M | Polyester | Silica Gel | None | Regen cellulose | Polyester |

As indicated hereinabove in Table 2, the individual zones comprise materials such as polyester, acidic alumina, glass fiber, alumina neutral, 90 um polyethylene (PE), PVDF, diatomaceous earth, regenerated (Regen) cellulose, silica gel, and a retainer ring. Table 3 describes the materials:

TABLE 3

Description of Material Layers in Filtration Wells

| Filter Type | Description: | Pore Size | Particle Size | Surface Area |
|---|---|---|---|---|
| Polyester | See Below** | | | |
| Acidic Alumina | Acidic Alumina | | 40-63 um | 150-155 m2/gm |
| Alumina Neut. | Neutral Alumina | | 40-63 um | 100 m2/gm |

TABLE 3-continued

| | | | | |
|---|---|---|---|---|
| 90 um PE | Porous polyethylene sheets | 90 um | Thickness 0.052 in--0.072 in | |
| Glass Fiber | Glass Fiber | 1.5 | 3.1 um | |
| Diatom. Earth | Diatomatious Earth | | 5-106 um 5-25 um | N/A |
| Regen Cellulose | Regenerated cellulose membrane - Hydrophilic | 0.2 um-1 um | Thickness 75 um | |
| Glass Wool | | | | |
| Silica Gel | Silica gel | 60A | 40-63 um | |
| PVDF | Polypropylene with hydrophilic PVDF Filtration area 0.1 m$^2$, height 0.6 inch width 0.2 inch | 0.1 to 0.65 um | | |
| Polyethylene | Porous polyethylene sheets | 90-130 um | | | um—micron
**Polyester Composition:

| Component | CAS No. | Percent by Weight, wt-% |
|---|---|---|
| Talc | 14807- | 5-35 |
| Polyester Fibers | Mixture | 5-45 |
| Cured Resin | Mixture | 4-40 |
| Polyester Scrim Backing | Mixture | 0-25 |
| Nylon Film Backing | Mixture | 0-35 |
| Fiberglass or Steel Core | Mixture | 0-10 |

The objective of Example 1 was to screen a series of filtration well configurations by comparing the mass of pelleted material from filtered samples with the mass of pelleted material following conventional centrifugation. The individual well filter types A-M employed standard centrifuge microtube (1.5 ml to 2.0 ml) or spin tube. The amount of material provided in the deep bed filtration zone of each spin tube ranged from about 150 to about 200 mg and a particle size from about 10 to about 106 um effective to provide course separation of course particles of insoluble proteins and protein fragments from a mixture of interacting proteins, insoluble protein fragments, and protein fragments in a buffer solution.

According to the procedure of the current invention, each well filter run consisted of the following steps:

Haploid yeast cells genomically tagged with Protein A at the Nup53 allele (NUP53-PrA, as Alber et al. Nature (2007) vol. 450 (7170) pp. 695-701) were cryogenically disrupted with a Ball Mill (e.g. RETCH PM 100 or MM 301, Available from Retsch GmbH, Haan, Germany) or a mortar grinder to provide a Nup53-PrA yeast cell powder at cryogenic conditions. Each sample 100 mg of the Nup53-Pra powder material was solubilized with 350 uL of a buffered solution (extraction buffer) consisting of 40 mM Tris (tris(hydroxymethyl)glycine), 250 mM trisodium citrate, 150 mM sodium chloride, 1% v/v TRITON X-100 (polyethylene glycol mono [4-(1,1,3,3-tetramethylbutyl)phenyl ether, Available from Acros Organics and Fisher Scientific), and protease inhibitors (Available from Sigma-Aldrich). For each well filter A-M-type tested, 350 uL of the buffered Nap53 solution sample, prepared as above, was pipetted into each individual filtration well or tube. Each of the individual filtration wells was spun in a BECKMAN ALLEGRA 6R centrifuge with a GH-3.8 rotor (Available from Beckman Coulter, Inc., California) at 3000 rpm (about 2100 RCF), at 4° C., for 20 minutes. Each filtrate was collected in a collection tube. A control sample was clarified, without filtration, by centrifugation for 20 minutes at 14000 RPM (about 20,800 RCF) at 4° C. in an EPPENDORF 5417 R MICROFUGE w/F45-30-11 rotor (Available from Eppendorf International, Germany). Each filtrate collected was further centrifuged in the same manner as the control (centrifuge only) sample. The weights of the pellets obtained upon filtration followed by centrifugation (using each different configuration, respectively), were compared to the weight of a pellet obtained by centrifugation only. The difference between the two pellet masses was taken as the measure of material removed from the buffered solution by the filter—as a substitute for centrifugation.

Tubes F and I showed the best performance based on retention of insolubles as shown in Table 4 hereinbelow:

TABLE 4

Example 1 Performance Results

| Code | Tube (mg) | Tube + Pellet | Diff., mg | % Centrifuged |
|---|---|---|---|---|
| F | 1012.4 | 1023.6 | 11.2 | 28 |
| I | 990.8 | 1014.9 | 24.1 | 60 |
| Centrifuged | 1098.3 | 11.38 | 40.5 | N/A |

The performance of the other individual filtration well configurations was shown to be insufficient based on their failure to retain the insoluble cell material.

Example 2

The filtrate material obtained from filtration wells F and I were compared with the supernatant from the centrifuged control sample of Example 1 to determine their relative performance in an affinity chromatography experiment. In Example 2, filtrates I and F were not further clarified by centrifugation, but used directly as material from which to purify Nup53-PrA. Each of the filtrates or centrifugal supernatant was transferred to tubes containing 10 uL of a slurry containing magnetic beads conjugated with rabbit IgG (Available from DYNAL, INVITROGEN, Life Technologies, California, USA). The magnetic beads were resuspended in the filtrate by inversion and incubated for 1 hour at 4° C. with continuous rotation. After incubation, the tubes were placed on a magnet and the beads were washed 3 times with 600 uL of the extraction buffer of Example 1. After washing each lot of beads was resuspended in the extraction buffer and transferred to a 0.2 mL microcentrofuge tube, respectively. Finally, each was eluted in 25 uL of LDS solution (lithium dodecyl sulfate, available from INVITROGEN, Life Technologies, California, USA) and incubated 10 minutes at RT with mechanical mixing. The tubes were placed on a magnet and the LDS solution removed, combined with a reducing agent, and heated at 75° C. for 10 minutes before being analyzed by SDS-PAGE (NuPAGE system, Available from INVITROGEN, Life Technologies, California). The comparison is shown in FIG. 6 which illustrates that the background pattern of the stain were substantially similar for the filtered samples F and I; despite being notably different from the centrifuged sample.

Figure 6:
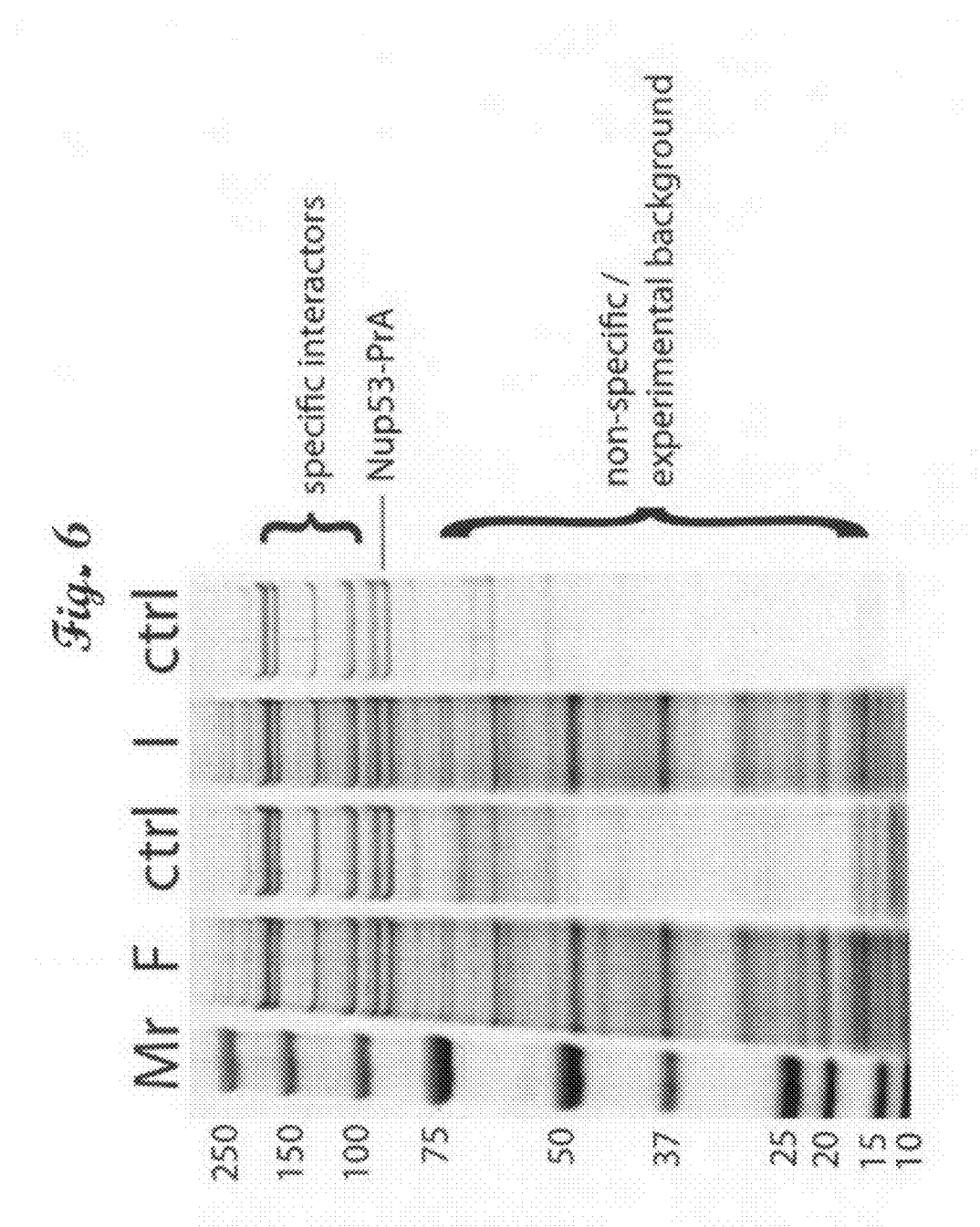
FIG. 6 shows a comparison of how example filtration devices F and I of the present invention compare to centrifugation.

FIG. 6 shows a comparison of filtration devices F and I to centrifugation (ctrl). Shown are LDS elutates from beads used for affinity chromatography (NupS3-PrA) carried out on lysates cleared by filtration (devices F or I) or centrifugation (two independent trials, labeled ctrl). Protein bands were visualized by COOMASSIE staining upon separation of the sample contents by SDS•PAGE. A molecular weight marker (Mr) is provided for orientation, with masses indicated in kDa. Labeled are two areas of the gel used for qualitative comparison: 1) a high molecular weight region where filtration and centrifugation yielded similar results, and here the material was known to be specific Nup53-associated proteins; and 2) a region on the gel where filtration differs from centrifugation, and where the material was most likely to be non-specific background due to inadequate clearance of the lysate by filtration.

Example 3

Following the procedure of Example 1, an additional set of filtration well structures T, U, V, and D were prepared as individual 2 mL spin tubes and compared with filtration wells A, I and F of Example 1 as the following series of individual well structures employing diatomaceous earth or silica gel with combinations of membranes. Each spin tube comprised from about 100 mg to about 300 mg of diatomaceous earth or silica gel with a particle size effective to provide 0.5 micron filtration clearance. The structures of the multi-layer filtration spin tubes of Example 3 are shown in Table 5. In spin tubes T, U, V and D, a retainer ring is placed at the top of the well and the deep bed filter matrix is indicated in the column headed, "Ret. Ring". In spin tubes A, F and I, no retainer ring is present and the column heading indicates the content of the intermediate layer. In wells A, F and I, the deep bed filter matrix materials were acidic alumina, diatomaceous earth, and silica gel, respectively.

TABLE 5

Structure of the Spin Tubes of Example 3 by Zone (Zn)

| Well No. | Sponge Zn | Deep Bed Filtration Zn | Ret. Ring Zn | Membrane Zn | Lower Bed Filtration Zn |
|---|---|---|---|---|---|
| T | Polyester | Diatom. Earth | Diatom. Earth | Glass Fiber | PVDF/ Polyester |
| U | Ret. Ring | Polyester | Diatom. Earth 300 mg | Glass Fiber | PVDF/ Polyester |
| V | Ret. Ring | Polyester | Diatom. Earth Fine | Glass Fiber | Polyester |
| D | Ret. Ring | Polyester | Diatom. Earth Fine | Glass Fiber | Polyester |
| A | Polyester | Acidic Alumina | None | Glass Fiber | Polyester |
| F | Polyester | Diatom. Earth | None | Glass Fiber | Polyester |
| I | Polyester | Silica Gel | None | PVDF | Polyester |

The results of the analysis of Example 3 are shown in the following Table 6.

TABLE 6

Results of Example 3 Spin Tubes T, U, V, W. F, and I:

| Code | Tube (mg) | Tube + Pellet | Diff., mg | % Centrifuged |
|---|---|---|---|---|
| T | 1004.5 | 1013.6 | 9.1 | 20 |
| U | 1015.6 | 1023.4 | 7.8 | 17 |
| V | 999.3 | 1024.4 | 16.4 | 36 |
| W | 1008.2 | 1046.0 | 38.4 | 84 |
| F | 990.2 | 1001.1 | 11 | 24 |
| I | 994.4 | 1030.2 | 35.8 | 78 |
| Centrifuged | 1099.5 | 1145.3 | 45.8 | N/A |

Figure 7:
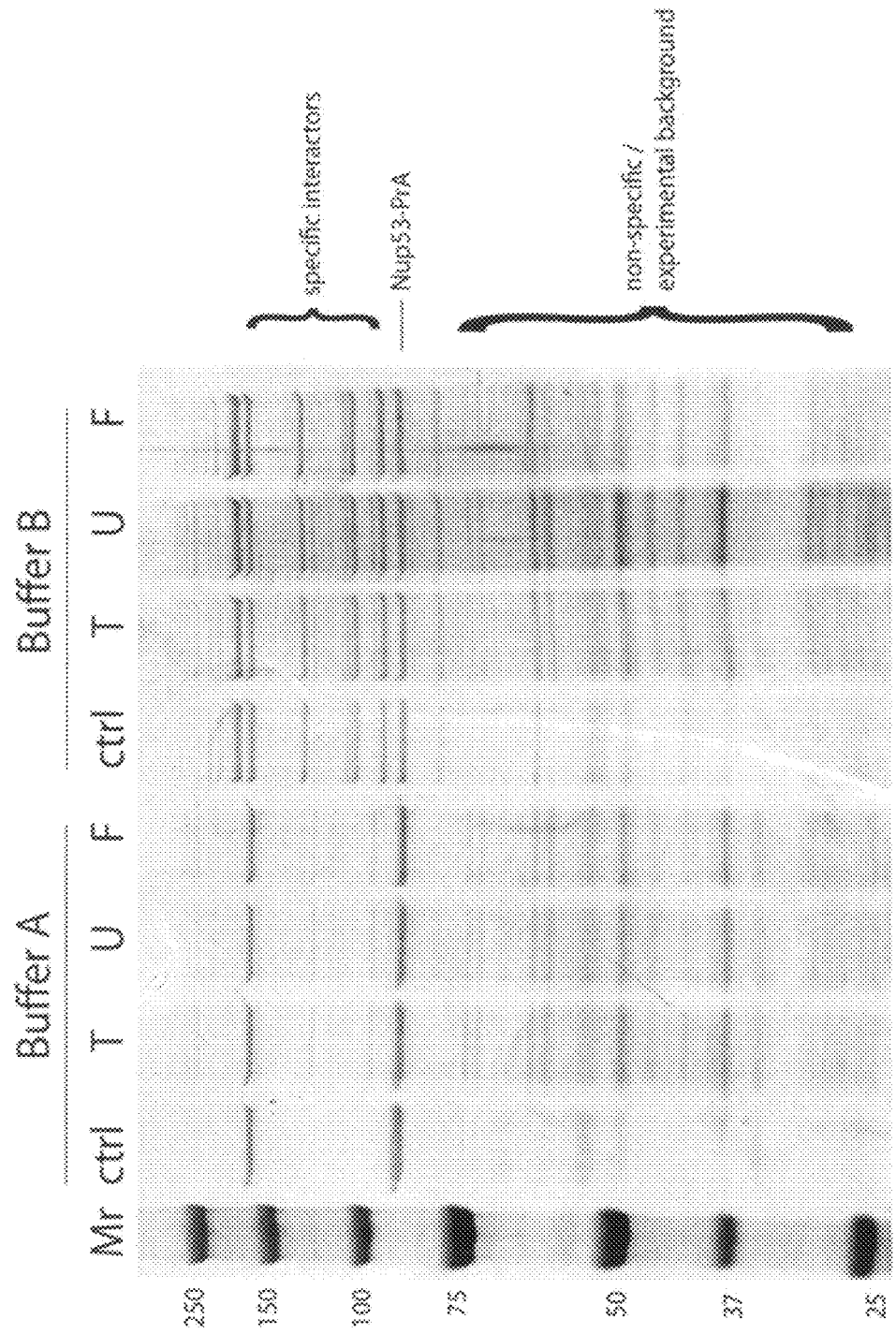
FIG. 7 represents a comparison of the Centrifuged Control to the filtered samples using devices T, U, and F.

The results in Table 6 showed that sample individual wells T, U and F provided the best performance. FIG. 7 represents a comparison of the Centrifuged control to the filtered samples using devices T, U, and F, by SDS-PAGE (sodium dodecyl sulfate-polyacrylamide gel electrophoresis, NuPAGE system, Available from INVITROGEN, Life Technologies, California). The experiments were carried out as described previously, but in this case two distinct solvents were used in two respective experiments: the previously used extraction buffer, and another buffer which differed in the amount of trisodium citrate (50 mM) and NaCl (300 mM) present. Gel electrophoresis images of the T, U and F samples showed that the results were all significantly similar to the centrifugation results as assessed by the quality of an affinity purification of Nup53-PrA.

FIG. 7. Shows a comparison of filtration devices T, U, F and to centrifugation (ctrl). Shown in FIG. 7 are LDS elutates from beads used for affinity chromatography (Nup53-PrA) carried out on lysates cleared by filtration (devices F or I) or centrifugation (ctrl), in two different buffer systems:
A: 40 mM Tris pH 8.0, 50 mM trisodium citrate, 300 mM NaCl. 1% v/v TRITON X-100; and
B: 40 mM Tris pH 8.0, 250 mM trisodium citrate, 150 mM NaCl. 1% v/v TRITON X-100.

Protein bands were visualized by COOMASSIE staining upon separation of the sample contents by SDS-PAGE. A molecular weight marker (Mr) was provided for orientation, with masses indicated in kDa. In FIG. 7, two areas of the gel used for qualitative comparison are labeled as in FIG. 6. In this Example 3, a significant improvement in the quality of the filtrates relative to the centrifuged samples (Compare to FIG. 6 of Example 2.) was observed.

Example 4

96 Well Filter Plate

A performance test was made using of a 96 well filter plate having the structure shown in Table 7, hereinbelow. The materials shown in Table 7 include polyester, diatomaceous earth, and PVDF membrane as defined in Table 2 of Example 1. In order to avoid channeling and provide a more even distribution through the filtration well, the retainer ring was provided between the diatomaceous earth layer and the PVDF membrane. Each well of the 96 well filter plate was prepared adding each of the materials shown in Table 7 to the each well in the order from bottom to top and pressing or pressing each material firmly into each well as shown in Table 7, with reference to FIG. 2. The lower bed filtration media 250 comprising polyester as defined hereinabove in Table 7 was pressed into each well to a height of about 0.5 cm. A membrane layer 250 of PVDF was pressed in place over the lower bed filtration media. The PVDF comprised polypropylene with a hydrophilic PVDF filtration area of 0.1 m² and having a height of 0.6 inches. A retainer ring 230 comprising polypropylene, of ⅟₃₂ inch in height, was pressed in place over the membrane layer to prevent lysate channeling in the individual filter well. The Deep Bed Filtration zone 215 was filled with 400 mg of diatomaceous earth and pressed in place over the retainer ring. The polyester material as defined hereinabove in Table 3 was pressed in place over the Deep Bed Filtration zone 215 to a height of about 0.5 cm to form the Sponge Zone 210. An upper collection zone 205 being a void space of about 1200 uL (microliters) above the sponge zone was maintained to permit the introduction of liquid samples for analysis.

TABLE 3

96 Well Filter Plate Structure (With Reference to FIG. 2)

| Reference No. | Contents | Filtration Porosity, um |
|---|---|---|
| 205 | Upper Collection Zone | (Void) N/A |
| 210 | Sponge zone, Polyester | |
| 215 | Deep bed filtration zone, Diatomaceous Earth | |
| 230 | Retainer Ring | |
| 240 | Membrane, PVDF | 0.2 micron |
| 250 | Lower Bed filtration media, Polyester | |

According to the procedure described herein above in Example 3, a 150 mg sample of a yeast material expressing Nup1-PrA (Disclosed in Alber et al. Nature (2007) vol. 450 (7170) pp. 695-701.) was dispensed in each well across a 96-well collection plate. 600 uL of each buffered extraction solvent, the 96 different buffer solvents comprising the compositions in the buffer array of solvents shown in FIG. 4, respectively.

Figure 8:
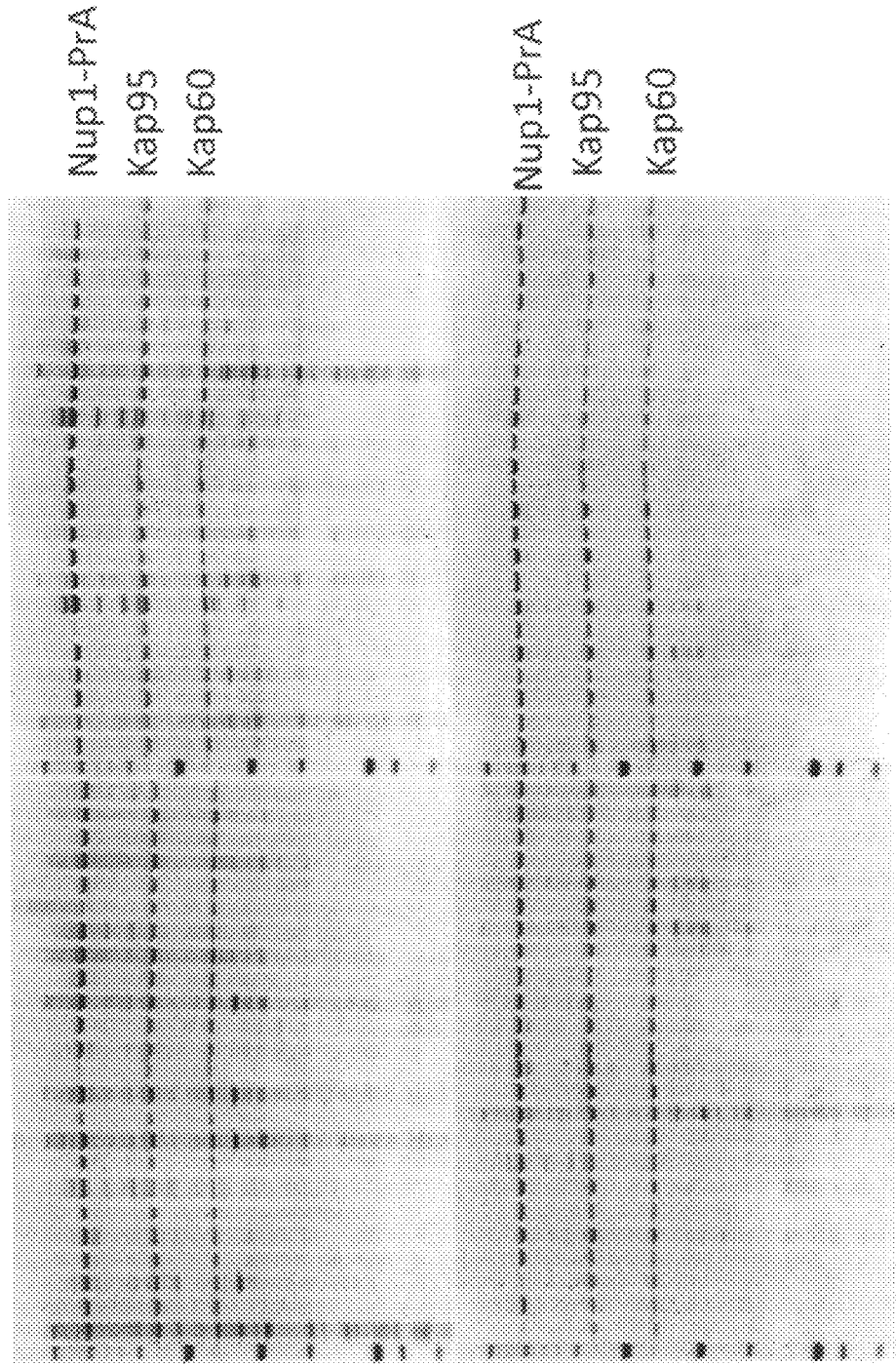
FIG. 8 shows an example of results of the 96-well device for an analysis of Nup1-PrA powder using the buffer array of capture solvents shown in FIG. 4.

The collection plate was covered and sonicated in a SONICATOR water bath sonication device (Available from QSonica, LLC, Connecticut, USA) followed by mechanical agitation to suspend the powder in the buffered extraction solvents. The resulting suspensions were individually transferred to a 96-well format filter plate, each well having the structure shown in Table 7. The 96-well filter was spun for about 5 minutes at 3.5 k rpm (corresponding to ~3 k RFC) on a JS-5.3 rotor (Available from Beckman Coulter, Inc., California). The liquid filtrates from the 96-well filter were collected in a second collection tray having 96 corresponding cells. Each cell of the second collection plate contained 5 ul slurry of rabbit IgG-conjugated magnetic beads (DYNABEADS, Available from INVITROGEN, Life Technologies, California). The second collection tray was agitated to resuspend the magnetic beads, and batch binding was allowed to proceed for 1 hr at 4° C. with rotational mixing. The beads in each well were washed 2 times with 500 uL of the corresponding buffer of extraction, and then resuspended in about 180 uL of the corresponding buffer of extraction and transferred to a 0.45 um filter plate and cleared through the wells by centrifugation, 5 minutes at 3 k in JS-5.3 rotor. An elution solution of 18 uL of LDS (NuPAGE loading buffer, available from INVITROGEN, Life Technologies, California) was added to the sample and they were subjected to mechanical agitation for 10 minutes at room temperature (Shiva Shaker, Available from Orochem, Lombard, Ill.) and then the elution was collected by centrifugation (in a final collection plate with DTT, dithiothreitol) 5 minutes at 3 k rpm in the JS-5.3 rotor (as above). The collected samples were heated 10 minutes at 75 degrees C. and analyzed by SDS-PAGE (4-12% Bis-Tris, NuPAGE, Available from INVITROGEN, Life Technologies, California) and COOMASSIE BLUE G250 staining (Available from INVITROGEN, Life Technologies, California). The results of the 96-well analysis of the Nup1-PrA powder using the buffer array shown in FIG. 4 are shown in FIG. 8 as LDS elutates from beads used for affinity chromatography (Nup1-PrA) carried out on lysate samples cleared by filtration from the 96-well filter. Protein bands are visualized by COOMASSIE staining upon separation of the sample contents by SDS-PAGE. The results show a range of different purification profiles. The two strongest physiological interactors are shown appearing in all of the wells. This result suggests that none of the extraction solvents and conditions used in the array of solvents shown in FIG. 4 were sufficient to destroy interfaces between the high affinity interactors, and that in several lanes or wells, new interactors Kap 95 and Kap 60 were observed. The array of results of Example 4 shown in FIG. 8 is consistent with and equivalent to a series of individual determinations using affinity chromatography with the same buffer solutions using conventional high speed centrifugation in a serial manner.

The invention claimed is:

1. A multi-well filter plate for the simultaneous and parallel purification and analysis of interacting proteins by affinity chromatography, said multi-well filter plate being adapted for separation of interacting proteins from a mixture of interacting proteins, insoluble protein fragments, and protein fragments by low speed centrifugation or positive pressure and comprising a plurality of filtration wells, each filtration well consisting of
   an upper sample zone;
   a lower filtration zone;
   a conical flow director zone; and,
   an elution tip,
   wherein the upper sample zone and the lower filtration zone are separated by a retainer ring disposed within the lower filtration zone, the retainer permitting fluid communication between the upper sample zone and the lower filtration zone;
   wherein said upper sample zone comprises an upper collection zone, a sponge zone comprising a depth filter media consisting of polyester, and a deep bed filtration zone comprising a deep bed filter matrix selected from the group consisting of diatomaceous earth and silica gel; and,
   wherein the lower filtration zone comprises the retainer ring, a supported hydrophilic membrane comprising polyester with hydrophilic PVDF or polypropylene with hydrophilic PVDF, and-a lower bed filtration media selected from the group consisting of none or polyester, and wherein the retainer ring is an o-ring comprising polypropylene or polyethylene, and optionally disposing a second retainer ring below the lower bed filtration media to support the supported hydrophilic membrane;
   whereby interacting proteins collected from each filtration well without further clarification by centrifugation are directly bound with affinity beads.

2. The multi-well filter plate for the simultaneous and parallel purification and analysis of interacting proteins by affinity chromatography of claim 1, wherein the plurality of filtration wells comprises 96 filtration wells.

3. The multi-well filter plate for the simultaneous and parallel purification and analysis of interacting proteins by affinity chromatography of claim 1, wherein the supported hydrophilic membrane consists of polypropylene with hydrophilic PVDF.

4. The multi-well filter plate for the simultaneous and parallel purification and analysis of interacting proteins by affinity chromatography of claim 1, wherein the supported hydrophilic membrane has a hydrophilic membrane porosity of from about 0.2 to about 0.45 um.

5. The multi-well filter plate for the simultaneous and parallel purification and analysis of interacting proteins by affinity chromatography of claim 1, wherein the deep bed filter matrix consists of diatomaceous earth.

6. The multi-well filter plate for the simultaneous and parallel purification and analysis of interacting proteins by affinity chromatography of claim 5, wherein the diatomaceous earth has a particle size of from about 5 to about 105 um.

7. The multi-well filter plate for the simultaneous and parallel purification and analysis of interacting proteins by affinity chromatography of claim 5, wherein the diatomaceous earth has a particle size of from about 5 to about 25 um.

8. The multi-well filter plate for the simultaneous and parallel purification and analysis of interacting proteins by affinity chromatography of claim 1, wherein the sponge zone provides a depth filter effective to provide a tortuous path to filter coarse particles of insoluble proteins and protein fragments from a mixture of a mixture of the interacting proteins, insoluble protein fragments, protein fragments and a buffer solution.

9. The multi-well filter plate for the simultaneous and parallel purification and analysis of interacting proteins by affinity chromatography of claim 1, wherein the sponge zone comprises a depth filter media consists of polyester.

10. A multi-well filter plate for the simultaneous and parallel purification and analysis of interacting proteins by affinity chromatography, said multi-well filter plate being adapted for separation of interacting proteins from a mixture of interacting proteins, insoluble protein fragments, and protein fragments by low speed centrifugation or positive pressure and comprising a plurality of filtration wells, each filtration well, consisting of
   an upper sample zone;
   a lower filtration zone;
   a conical flow director zone; and,
   an elution tip,
   wherein the upper sample zone and the lower filtration zone are separated by a retainer ring disposed within the lower filtration zone, the retainer permitting fluid communication between the upper sample zone and the lower filtration zone;
   wherein said upper sample zone comprises an upper collection zone, a sponge zone comprising a depth filter media consisting of polyester, and a deep bed filtration zone comprising a deep bed filter matrix consisting of diatomaceous earth; and,
   wherein the lower filtration zone comprises the retainer ring, a supported hydrophilic membrane consisting of polypropylene with hydrophilic PVDF, and a lower bed filtration media, wherein the retainer ring is an o-ring comprising polypropylene, and, wherein the lower bed filtration media is selected from the group consisting of none and polyester, and disposing a second retainer ring below the lower bed filtration media to support the supported hydrophilic membrane whereby interacting proteins collected from each filtration well without further clarification by centrifugation are directly bound with affinity beads.

11. The multi-well filter plate for the simultaneous and parallel purification and analysis of interacting proteins by affinity chromatography of claim 1, wherein the upper collection zone has a void space volume which is equal to or greater than a filter space volume, wherein the filter space volume comprises the sponge zone, the deep bed filtration zone, and the lower filtration zone.

12. The multi-well filter plate for the simultaneous and parallel purification and analysis of interacting proteins by affinity chromatography of claim 1, wherein the upper collection zone has a void space volume of from 600 to 1200 microliters.

13. The multi-well filter plate for the simultaneous and parallel purification and analysis of interacting proteins by affinity chromatography of claim 1, wherein the upper collection zone has a void space volume of from 750 to 1000 microliters.

14. The multi-well filter plate for the simultaneous and parallel purification and analysis of interacting proteins by affinity chromatography of claim 1, wherein plurality of filtration wells is selected from the group consisting of 6, 24, 96, and 192 filtration wells.

15. The multi-well filter plate for the simultaneous and parallel purification and analysis of interacting proteins by affinity chromatography of claim 1, wherein low speed centrifugation comprises centrifugation rates of from 1500 to 2500 g.

16. The multi-well filter plate for the simultaneous and parallel purification and analysis of interacting proteins by affinity chromatography of claim 1, wherein the positive pressure applied to the upper sample zone ranges from about 40 to about 60 psig.

17. The multi-well filter plate for the simultaneous and parallel purification and analysis of interacting proteins by affinity chromatography of claim 1, wherein the upper sample zone has a square cross section and the lower filtration zone has a cylindrical cross section.

18. A kit for the simultaneous and parallel purification and analysis of interacting proteins in an affinity chromatography process, said kit comprising at least one or more of the following:
   a. a collection plate having an array of individual collection zones,
   b. buffer plate having an array of solvent reservoirs corresponding the array of individual collection zones in the collection plate,
   c. a multi-well filter plate being adapted for separation of interacting proteins from a mixture of interacting proteins, insoluble protein fragments, and protein fragments by low speed centrifugation or positive pressure comprising a plurality of filtration wells, each filtration well being aligned with the array of individual collection zones of the collection plate, wherein each filtration well consists of an upper sample zone, a lower filtration zone, a conical flow director zone, and an elution tip, said upper sample zone and said lower filtration zone being separated by a retainer ring disposed within the lower filtration zone, said retainer ring permitting fluid communication between said upper sample zone and said lower filtration zone, said upper sample zone comprising an upper collection zone, a sponge zone comprising a depth filter media consisting of polyester, and a deep bed filtration zone comprising a deep bed filter matrix consisting of diatomaceous earth, said lower filtration zone comprising the retainer ring, a supported hydrophilic membrane consisting of polypropylene with hydrophilic PVDF, and a lower bed filtration media selected from the group consisting of none and polyester, and optionally a second retainer ring is disposed below the lower bed filtration media to support the supported hydrophilic membrane, wherein said first and second retainer rings are o-rings comprising polypropylene or polyethylene whereby interacting proteins collected from each filtration well without further clarification by centrifugation are directly bound with affinity beads; and
   d. a removable cover plate adapted to sealably cover the individual collection zones of the collection plate.

19. The kit for the simultaneous and parallel purification and analysis of interacting proteins in an affinity chromatography process of claim 18, wherein the array of solvent reservoirs contains aqueous solvents wherein each of the solvent reservoirs contains buffer solvent comprising water and a buffering agent or at least one salt or at least one detergent.

20. The kit for the simultaneous and parallel purification and analysis of interacting proteins in an affinity chromatography process of claim 19, wherein the buffer solvent comprises a buffering agent having a concentration range effective to equilibrate dispersed and/or at least partially solubilized cell extract.

21. The kit for the simultaneous and parallel purification and analysis of interacting proteins in an affinity chromatography process of claim 19, wherein the at least one salt is a chaotropic salt or a kosmotropic salt, or a combination of thereof.

22. The kit for the simultaneous and parallel purification and analysis of interacting proteins in an affinity chromatography process of claim 19, wherein the at least one salt is a single salt having both a choatropic component and a kosmotropic component.

23. The kit for the simultaneous and parallel purification and analysis of interacting proteins in an affinity chromatography process of claim 19, wherein the at least one detergent is selected from the group consisting of a nonionic detergent, an ionic detergent, and a zwitterionic detergent.

24. The kit for the simultaneous and parallel purification and analysis of interacting proteins in an affinity chromatography process of claim 19, wherein the buffering agent is selected from the group consisting of ammonium acetate, 4-2-hydroxyethyl-1-piperazine ethane sulfonic acid, and (hydroxymethyl)methylamine; the at least one salt is selected from the group consisting of potassium acetate, trisodium citrate, potassium chloride, and sodium chloride; and, the at least one detergent is selected from the group consisting of polyethylene glycol mono [4-(1,1,3,3-tetramethylbutyl)phenyl]ether, polyoxyethylene-20-sorbitane monolaurate, and 3-[(3-cholamidopropyl)dimethylammonio]-1-propanesulfonate.

25. The kit for the simultaneous and parallel purification and analysis of interacting proteins in an affinity chromatography process of claim 18, wherein the buffer plate is a 96-well format, wherein each of the reservoirs contains a buffer solvent composition according to the array shown in FIG. 4 wherein solvent composition of each reservoir of the array is indicated by the following symbol:

| Symbol | Chemical Name |
| --- | --- |
| A | Ammonium Acetate, $CH_3COONH_4$ |
| B | 4-2-hydroxyethyl-1-piperazine ethane sulfonic acid |
| C | Tris(hydroxymethyl)methylamine |
| D | Potassium Acetate, $CH_3CO_2K$ |
| E | Trisodium Citrate |
| F | Potassium Chloride |
| G | Sodium Chloride |
| H | Polyethylene glycol mono [4-(1,1,3,3-tetramethylbutyl)phenyl] ether |
| I | Polyoxyethylene-20-sorbitane monolaurate |
| J | 3-[(3-cholamidopropyl) dimethylammonio]-1-propanesulfonate |

26. The kit for the simultaneous and parallel purification and analysis of interacting proteins in an affinity chromatography process of claim 18, further comprising a second filter plate for separating washed affinity beads, a third collection plate for retaining affinity beads on elution, and a second collection plate for collecting eluted material.

27. The kit for the simultaneous and parallel purification and analysis of interacting proteins in an affinity chromatography process of claim 18, wherein the array of individual collections zones comprises 6, 24, 96, or 192 individual collection zones.

28. The kit for the purification and analysis of interacting proteins in an affinity chromatography process of claim 18, wherein the individual collection zones of the collection plate have a lower closed end and an upper open end and a cross section of the lower closed end has a u-shape or a v-shape.

29. A single barrel filtration well for separation of interacting proteins from a mixture of interacting proteins, insoluble protein fragments, and protein fragments and purification and analysis of interacting proteins by affinity chromatography, said single barrel filtration well consisting of:
an upper sample zone;
a lower filtration zone;
a conical flow director zone; and,
an elution tip;
wherein the upper sample zone and the lower filtration zone are separated by a retainer ring disposed within the lower filtration zone, the retainer ring permitting fluid communication between the upper sample zone and the lower filtration zone;
wherein said upper sample zone comprises an upper collection zone, a sponge zone, and a deep bed filtration zone;
wherein said sponge zone comprises a depth filter media consisting of polyester, and said deep bed filtration zone comprises a deep bed filter matrix selected from the group consisting of diatomaceous earth and silica gel;
wherein the lower filtration zone comprises the retainer ring comprising polypropylene or polyethylene, a supported hydrophilic membrane comprising polyester with hydrophilic PVDF or polypropylene with hydrophilic PVDF having a hydrophilic membrane porosity of from about 0.2 to about 0.45 um, and a lower bed filtration media selected from the group consisting of none and polyester, and optionally, a second retainer ring disposed below the lower bed filtration media to support the supported hydrophilic membrane; and,
wherein the upper collection zone has a void space volume which is equal to or greater than a filter space volume, wherein the filter space volume comprises the sponge zone, the deep bed filtration zone, and the lower filtration zone, whereby interacting proteins collected from each filtration well without further clarification by centrifugation are directly bound with affinity beads.

30. A multi-well filter plate for purification and analysis of interacting proteins by affinity chromatography comprising 2×3, 4×6, 8×12, or 2(8×12) rectangular arrays of the single barrel filtration well of claim 29 adapted to be disposed in said rectangular arrays to form the multi-well filter plate.

* * * * *